United States Patent
Bourque

(10) Patent No.: US 11,944,799 B2
(45) Date of Patent: Apr. 2, 2024

(54) GENERATING ARTIFICIAL PULSE

(71) Applicant: TC1 LLC, St. Paul, MN (US)

(72) Inventor: Kevin Bourque, Reading, MA (US)

(73) Assignee: TC1 LLC, St. Paul, MN (US)

( * ) Notice: Subject to any disclaimer, the term of this patent is extended or adjusted under 35 U.S.C. 154(b) by 188 days.

(21) Appl. No.: 17/103,283

(22) Filed: Nov. 24, 2020

(65) Prior Publication Data

US 2021/0077688 A1 Mar. 18, 2021

Related U.S. Application Data

(60) Continuation of application No. 16/055,471, filed on Aug. 6, 2018, now Pat. No. 10,881,772, which is a
(Continued)

(51) Int. Cl.
*A61M 60/148* (2021.01)
*A61M 60/178* (2021.01)
(Continued)

(52) U.S. Cl.
CPC ........ *A61M 60/148* (2021.01); *A61M 60/178* (2021.01); *A61M 60/216* (2021.01); *A61M 60/515* (2021.01); *A61M 60/569* (2021.01); *A61M 60/822* (2021.01); *A61M 2205/04* (2013.01); *A61M 2205/3334* (2013.01);
(Continued)

(58) Field of Classification Search
CPC .. A61M 1/1086; A61M 1/1005; A61M 1/122; A61M 1/1029; A61M 2205/50; A61M 2205/3365; A61M 2205/52
See application file for complete search history.

(56) References Cited

U.S. PATENT DOCUMENTS

| 3,240,207 A | 3/1966 | Barker et al. |
| 3,911,897 A | 10/1975 | Leachman |

(Continued)

FOREIGN PATENT DOCUMENTS

| EP | 445782 | 8/1994 |
| EP | 499939 | 8/1994 |

(Continued)

OTHER PUBLICATIONS

English Translation (machine) of JP 2009-297174 (Year: 2009).*
(Continued)

*Primary Examiner* — Brian T Gedeon
(74) *Attorney, Agent, or Firm* — Kilpatrick Townsend & Stockton LLP

(57) ABSTRACT

Mechanical circulatory assist systems and related methods produce a pulsatile blood flow in synchronization with heart activity. A mechanical circulatory assist system includes a continuous-flow pump and a controller. The continuous-flow pump is implantable in fluid communication with a left ventricle of a heart of a patient and an aorta of the patient to assist blood flow from the left ventricle to the aorta. The controller includes a sensor that generates a signal indicative of an activity of the heart. The controller is operatively connected to the continuous-flow pump and configured to operate the continuous-flow pump in an artificial pulse mode in synchronization with the activity of the heart.

26 Claims, 10 Drawing Sheets

Related U.S. Application Data continuation of application No. 15/785,097, filed on Oct. 16, 2017, now Pat. No. 10,086,122, which is a continuation of application No. 15/221,456, filed on Jul. 27, 2016, now Pat. No. 9,801,988, which is a continuation of application No. 14/592,630, filed on Jan. 8, 2015, now Pat. No. 9,433,717, which is a continuation of application No. 14/261,817, filed on Apr. 25, 2014, now Pat. No. 8,961,388, which is a continuation of application No. 13/926,044, filed on Jun. 25, 2013, now Pat. No. 9,011,312, which is a division of application No. 13/241,831, filed on Sep. 23, 2011, now Pat. No. 8,506,471.

(60) Provisional application No. 61/386,018, filed on Sep. 24, 2010.

(51) Int. Cl.
*A61M 60/216* (2021.01)
*A61M 60/515* (2021.01)
*A61M 60/546* (2021.01)
*A61M 60/569* (2021.01)
*A61M 60/822* (2021.01)

(52) U.S. Cl.
CPC .............. *A61M 2205/3365* (2013.01); *A61M 2205/3507* (2013.01); *A61M 2205/50* (2013.01); *A61M 2205/52* (2013.01); *A61M 2210/12* (2013.01)

(56) References Cited

U.S. PATENT DOCUMENTS

| | | | |
|---|---|---|---|
| 4,190,057 | A | 2/1980 | Hill et al. |
| 4,296,500 | A | 10/1981 | Monties et al. |
| 4,600,855 | A | 7/1986 | Strachan |
| 4,957,504 | A * | 9/1990 | Chardack ............ A61M 60/569 600/16 |
| 5,139,517 | A | 8/1992 | Corral |
| 5,279,292 | A | 1/1994 | Baumann et al. |
| 5,289,821 | A | 3/1994 | Swartz |
| 5,290,227 | A * | 3/1994 | Pasque ................ A61M 60/422 623/3.13 |
| 5,318,592 | A | 6/1994 | Schaldach |
| 5,385,581 | A | 1/1995 | Bramm et al. |
| 5,503,615 | A | 4/1996 | Goldstein |
| 5,658,318 | A | 8/1997 | Stroetmann et al. |
| 5,693,091 | A | 12/1997 | Larson et al. |
| 5,715,837 | A | 2/1998 | Chen |
| 5,725,357 | A | 3/1998 | Nakazeki et al. |
| 5,798,454 | A | 8/1998 | Nakazeki et al. |
| 5,807,258 | A | 9/1998 | Cimochowski et al. |
| 5,888,242 | A | 3/1999 | Antaki et al. |
| 5,947,703 | A | 9/1999 | Nojiri et al. |
| 6,027,498 | A | 2/2000 | Mutch et al. |
| 6,048,363 | A | 4/2000 | Nagyszalanczy et al. |
| 6,053,873 | A | 4/2000 | Govari et al. |
| 6,066,086 | A | 5/2000 | Antaki et al. |
| 6,139,487 | A | 10/2000 | Siess |
| 6,142,752 | A | 11/2000 | Akamatsu et al. |
| 6,146,325 | A | 11/2000 | Lewis et al. |
| 6,171,253 | B1 | 1/2001 | Bullister et al. |
| 6,176,822 | B1 | 1/2001 | Nix et al. |
| 6,264,601 | B1 | 7/2001 | Jassawalla et al. |
| 6,264,635 | B1 | 7/2001 | Wampler et al. |
| 6,277,078 | B1 | 8/2001 | Porat et al. |
| 6,293,901 | B1 | 9/2001 | Prem |
| 6,367,333 | B1 | 4/2002 | Bullister et al. |
| 6,395,027 | B1 | 5/2002 | Snyder |
| 6,409,674 | B1 | 6/2002 | Brockway et al. |
| 6,422,990 | B1 | 7/2002 | Prem |
| 6,443,884 | B1 | 9/2002 | Miyawaki |
| 6,468,041 | B2 | 10/2002 | Ozaki |
| 6,481,292 | B1 | 11/2002 | Reich |
| 6,540,658 | B1 | 4/2003 | Fasciano et al. |
| 6,547,753 | B1 | 4/2003 | Plunkett et al. |
| 6,575,717 | B2 | 6/2003 | Ozaki et al. |
| 6,585,635 | B1 | 7/2003 | Aldrich |
| 6,589,030 | B2 | 7/2003 | Ozaki |
| 6,605,032 | B2 | 8/2003 | Benkowski et al. |
| 6,623,420 | B2 | 9/2003 | Reich et al. |
| 6,626,644 | B2 | 9/2003 | Ozaki |
| 6,636,769 | B2 | 10/2003 | Govari et al. |
| 6,669,624 | B2 | 12/2003 | Frazier |
| 6,688,861 | B2 | 2/2004 | Wampler |
| 6,707,200 | B2 | 3/2004 | Carroll et al. |
| 6,716,189 | B1 | 4/2004 | Jarvik et al. |
| 6,736,980 | B2 | 5/2004 | Moscaritolo |
| 6,742,999 | B1 | 6/2004 | Nüsser et al. |
| 6,817,836 | B2 | 11/2004 | Nose et al. |
| 6,890,303 | B2 | 5/2005 | Fitz |
| 6,949,066 | B2 | 9/2005 | Bearnson et al. |
| 6,969,345 | B2 | 11/2005 | Jassawalla et al. |
| 6,974,436 | B1 | 12/2005 | Aboul-Hosn et al. |
| 6,984,201 | B2 | 1/2006 | Khaghani et al. |
| 6,991,595 | B2 | 1/2006 | Burke et al. |
| 7,029,433 | B2 | 4/2006 | Chang |
| 7,138,776 | B1 | 11/2006 | Gauthier et al. |
| 7,147,604 | B1 | 12/2006 | Allen et al. |
| 7,150,711 | B2 | 12/2006 | Nusser et al. |
| 7,160,242 | B2 | 1/2007 | Yanai |
| 7,175,588 | B2 | 2/2007 | Morello |
| 7,211,048 | B1 | 5/2007 | Najafi et al. |
| 7,229,474 | B2 | 6/2007 | Hoffmann et al. |
| 7,239,098 | B2 | 7/2007 | Masino |
| 7,284,956 | B2 | 10/2007 | Nose et al. |
| 7,320,706 | B2 | 1/2008 | Al-Najjar |
| 7,396,327 | B2 | 7/2008 | Morello |
| 7,462,019 | B1 | 12/2008 | Allarie et al. |
| 7,497,116 | B2 | 3/2009 | Miyakoshi et al. |
| 7,511,443 | B2 | 3/2009 | Townsend et al. |
| 7,520,850 | B2 | 4/2009 | Brockway |
| 7,578,782 | B2 | 8/2009 | Miles et al. |
| 7,591,777 | B2 | 9/2009 | LaRose |
| 7,645,225 | B2 | 1/2010 | Medvedev et al. |
| 7,645,255 | B2 | 1/2010 | Gordon et al. |
| 7,699,588 | B2 | 4/2010 | Mendler |
| 7,850,594 | B2 | 12/2010 | Sutton et al. |
| 7,854,631 | B2 | 12/2010 | Townsendl et al. |
| 7,861,582 | B2 | 1/2011 | Miyakoshi et al. |
| 7,887,479 | B2 | 2/2011 | LaRose et al. |
| 7,951,062 | B2 | 5/2011 | Morello |
| 7,963,905 | B2 | 6/2011 | Salmonsen et al. |
| 7,976,271 | B2 | 7/2011 | LaRose et al. |
| 7,988,728 | B2 | 8/2011 | Ayre |
| 7,998,054 | B2 | 8/2011 | Bolling |
| 8,043,074 | B2 * | 10/2011 | Tada .................... A61M 60/824 417/423.12 |
| 8,123,669 | B2 | 2/2012 | Siess et al. |
| 8,157,720 | B2 | 4/2012 | Marseille et al. |
| 8,246,530 | B2 | 8/2012 | Sullivan |
| 8,303,482 | B2 | 11/2012 | Schima et al. |
| 8,382,830 | B2 | 2/2013 | Maher et al. |
| 8,506,470 | B2 | 8/2013 | LaRose et al. |
| 8,506,471 | B2 | 8/2013 | Bourque |
| 8,517,699 | B2 | 8/2013 | Horvath |
| 8,556,795 | B2 | 10/2013 | Bolyard et al. |
| 8,597,350 | B2 | 12/2013 | Rudser et al. |
| 8,657,733 | B2 | 2/2014 | Ayre et al. |
| 8,657,875 | B2 | 2/2014 | Kung et al. |
| 8,764,621 | B2 | 7/2014 | Badstibner et al. |
| 8,771,165 | B2 | 7/2014 | Choi et al. |
| 8,852,099 | B2 | 10/2014 | Von Arx et al. |
| 8,870,739 | B2 | 10/2014 | LaRose et al. |
| 8,882,477 | B2 | 11/2014 | Fritz, IV et al. |
| 8,956,275 | B2 | 2/2015 | Bolyard et al. |
| 9,387,284 | B2 | 7/2016 | Heilman et al. |
| 9,433,714 | B2 | 9/2016 | Voskoboynikov et al. |
| 9,433,717 | B2 | 9/2016 | Bourque |
| 9,801,988 | B2 | 10/2017 | Bourque |
| 2002/0116055 | A1 | 8/2002 | Snyder |
| 2002/0183628 | A1 | 12/2002 | Reich et al. |

(56) References Cited

U.S. PATENT DOCUMENTS

| | | |
|---|---|---|
| 2003/0023255 A1 | 1/2003 | Miles et al. |
| 2003/0045772 A1 | 3/2003 | Reich et al. |
| 2003/0074144 A1 | 4/2003 | Freed et al. |
| 2003/0199727 A1 | 10/2003 | Burke et al. |
| 2004/0034272 A1 | 2/2004 | Diaz et al. |
| 2004/0064012 A1* | 4/2004 | Yanai .............. F04D 15/0209 600/16 |
| 2005/0071001 A1 | 3/2005 | Jarvik |
| 2005/0107658 A1 | 5/2005 | Brockway |
| 2005/0131271 A1 | 6/2005 | Benkowski et al. |
| 2005/0159639 A1 | 7/2005 | Skliar et al. |
| 2006/0047205 A1 | 3/2006 | Ludomirsky et al. |
| 2006/0155158 A1 | 7/2006 | Aboul-Hosn |
| 2006/0229488 A1 | 10/2006 | Ayre et al. |
| 2006/0241335 A1 | 10/2006 | Benkowski et al. |
| 2007/0073393 A1 | 3/2007 | Kung et al. |
| 2007/0083077 A1 | 4/2007 | Frazier |
| 2007/0142923 A1 | 6/2007 | Ayre et al. |
| 2007/0282210 A1 | 12/2007 | Stern |
| 2008/0154095 A1 | 6/2008 | Stubkjaer et al. |
| 2008/0281146 A1 | 11/2008 | Morello |
| 2008/0319544 A1 | 12/2008 | Yaegashi |
| 2009/0099406 A1 | 4/2009 | Salmonsen et al. |
| 2009/0138080 A1 | 5/2009 | Siess et al. |
| 2009/0156885 A1 | 6/2009 | Morello et al. |
| 2010/0130809 A1 | 5/2010 | Morello |
| 2010/0152526 A1 | 6/2010 | Pacella et al. |
| 2010/0222632 A1 | 9/2010 | Poirier |
| 2010/0222633 A1 | 9/2010 | Poirier |
| 2010/0222634 A1 | 9/2010 | Poirier |
| 2010/0222635 A1 | 9/2010 | Poirier |
| 2010/0222878 A1 | 9/2010 | Poirier |
| 2010/0241223 A1 | 9/2010 | Lee et al. |
| 2010/0327687 A1 | 12/2010 | Iannello et al. |
| 2011/0054239 A1 | 3/2011 | Sutton et al. |
| 2011/0071337 A1 | 3/2011 | Thompson et al. |
| 2011/0112354 A1 | 5/2011 | Nishimura et al. |
| 2011/0237863 A1 | 9/2011 | Ricci et al. |
| 2011/0313237 A1 | 12/2011 | Miyakoshi et al. |
| 2012/0078030 A1 | 3/2012 | Bourque |
| 2012/0078031 A1 | 3/2012 | Burke et al. |
| 2012/0226097 A1 | 9/2012 | Smith et al. |
| 2012/0245681 A1 | 9/2012 | Casas et al. |
| 2013/0331934 A1 | 12/2013 | Kabir et al. |
| 2014/0012067 A1 | 1/2014 | Poirier |
| 2014/0058190 A1 | 2/2014 | Gohean et al. |
| 2014/0100413 A1 | 4/2014 | Casas et al. |
| 2014/0194985 A1 | 7/2014 | Vadala, Jr. |
| 2014/0235931 A1 | 8/2014 | Bourque |
| 2014/0275723 A1 | 9/2014 | Fritz, IV et al. |
| 2014/0275727 A1 | 9/2014 | Bonde et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |
| 2015/0057488 A1 | 2/2015 | Yomtov |
| 2015/0151032 A1 | 6/2015 | Voskoboynikov et al. |
| 2015/0174307 A1 | 6/2015 | Eckman et al. |
| 2015/0328466 A1 | 11/2015 | Peters et al. |
| 2016/0058929 A1 | 3/2016 | Medvedev et al. |
| 2016/0058930 A1 | 3/2016 | Medvedev et al. |
| 2016/0101230 A1 | 4/2016 | Ochsner et al. |
| 2016/0193397 A9 | 7/2016 | Aber et al. |
| 2016/0263299 A1 | 9/2016 | Xu et al. |

FOREIGN PATENT DOCUMENTS

| | | | |
|---|---|---|---|
| EP | 1046403 | 10/2000 | |
| EP | 1354606 | 10/2003 | |
| EP | 2298375 | 3/2011 | |
| EP | 2618862 | 7/2013 | |
| EP | 2618863 | 7/2013 | |
| GB | 2152241 | 7/1985 | |
| JP | 58054929 | 4/1983 | |
| JP | 04504673 | 8/1992 | |
| JP | 09276397 | 10/1997 | |
| JP | 2002224066 | 8/2002 | |
| JP | 2003501180 | 1/2003 | |
| JP | 2004510482 | 4/2004 | |
| JP | 2005514962 | 5/2005 | |
| JP | 2008543378 | 12/2008 | |
| JP | 2009-297174 | * 12/2009 | .............. A61M 1/64 |
| JP | 2009297174 | 12/2009 | |
| JP | 2013540005 | 10/2013 | |
| JP | 2013540006 | 10/2013 | |
| JP | 2013240006 | 11/2013 | |
| TW | 201221160 | 6/2012 | |
| WO | 9215239 | 9/1992 | |
| WO | 9959652 | 11/1999 | |
| WO | 0069490 | 11/2000 | |
| WO | 0076288 | 12/2000 | |
| WO | 0076822 | 12/2000 | |
| WO | 0112070 | 2/2001 | |
| WO | 0172352 | 10/2001 | |
| WO | 03015609 | 2/2003 | |
| WO | 2004028593 | 4/2004 | |
| WO | 2005006975 | 1/2005 | |
| WO | 2005051838 | 6/2005 | |
| WO | 2006133409 | 12/2006 | |
| WO | 2009150893 | 12/2009 | |
| WO | 2010025411 | 3/2010 | |
| WO | 2010099411 | 9/2010 | |
| WO | 2012040544 | 3/2012 | |

OTHER PUBLICATIONS

Bullister et al., "Physiologic Control Algorithms for Rotary Blood Pumps using Pressure Sensor Input", Organs, vol. 26, No. 11, 2002, pp. 931-938.

Ednick et al., "Telemetric Recording of Intrapleural Pressure", Journal of Surgical Research, vol. 138, No. 1, 2007, pp. 10-14.

Ellozy et al., "First Experience in Human Beings with a Permanently Implantable Intrasac Pressure Transducer for Monitoring Endovascular Repair of Abdominal Aortic Aneurysms", J Vasc Surg., vol. 40, Sep. 2004, pp. 405-412.

Ferreira et al., "A Rule-Based Controller Based on Suction Detection for Rotary Blood Pumps", Conf Proc IEEE Eng Med Bioi Soc., 2007, pp. 3978-3981.

Fukamachi et al., "An Innovative, Sensorless, Pulsatile, Continuous-Flow Total Artificial Heart: Device Design and Initial In Vitro Study", The Journal of Heart and Lung Transplantation, vol. 29, No. 1, Jan. 2010, 20 pages.

Giridharan et al., "Control Strategy for Maintaining Physiological Perfusion with Rotary Blood Pumps", Artif Organs, vol. 27, No. 7, 2003, pp. 639-648.

Haj-Yahia , "Midterm Experience with the Jarvik 2000 Axial Flow Left Ventricular Assist Device", J Thorac Cardiovasc Surg., vol. 134, No. 1, 2007, pp. 199-203.

Ising et al., "Flow Modulation Algorithms for Continuous Flow Left Ventricular Assist Devices to Increase Vascular Pulsatility: A Computer Simulation Study", Cardiovascular Engineering and Technology, vol. 2, No. 2, Mar. 26, 2011, pp. 90-100.

Khalil et al., "Induced Pulsation of a Continuous-Flow Total Artificial Heart in a Mock Circulatory System", The Journal of Heart and Lung Transplantation, vol. 29, No. 5, May 2010, pp. 568-573.

Letsou et al., "Is Native Aortic Valve Commissural Fusion in Patients with Long-Term Left Ventricular Assist Devices Associated with Clinically Important Aortic Insufficiency", The Journal of Heart and Lung Transplantation, vol. 25, No. 4, Apr. 2006, pp. 395-399.

Ohuchi et al., "Control Strategy for Rotary Blood Pumps", Artif Organs, vol. 25, No. 5, May 2001, pp. 366-370.

Reesink et al., "Suction Due to Left Ventricular Assist: Implications for Device Control and Management", Artif Organs, vol. 31, No. 7, 2007, pp. 542-549.

Rozenman , "Wireless Acoustic Communication with a Miniature Pressure Sensor in the Pulmonary Artery for Disease Surveillance and Therapy of Patients with Congestive Heart Failure", Journal of the American College of Cardiology, vol. 49, No. 7, Feb. 20, 2007, pp. 784-789.

(56) References Cited

OTHER PUBLICATIONS

Shi et al., "Numerical Modeling of Hemodynamics with Pulsatile Impeller Pump Support", Annals of Biomedical Engineering, vol. 38, No. 8, Aug. 2010, pp. 2621-2634.
Shi et al., "Numerical Simulation of Cardiovascular Dynamics with Left Heart Failure and In-Series Pulsatile Ventricular Assist Device", Artificial Organs, vol. 30, No. 12, 2006, pp. 929-948.
Shiose et al., "Speed Modulation of the Continuous-Flow Total Artificial Heart to Simulate a Physiologic Arterial Pressure Waveform", ASAIO Journal, vol. 56, No. 5, 2010, pp. 403-409.
Travis et al., "Vascular Pulsatility in Patients with a Pulsatile- or Continuous-Flow Ventricular Assist Device", Journal of Thoracis and Cardiovascular Surgery, vol. 133, No. 2, Feb. 2007, pp. 517-524.
Tuzun et al., "The Effect of Intermittent Low Speed Mode upon Aortic Valve Opening in Calves Supported with a Jarvik 2000 Axial Flow Device.", ASAIO Journal, vol. 51, No. 2, 2005, pp. 139-143.
Vandenberghe et al., "Hemodynamic Modes of Ventricular Assist with a Rotary Blood Pump: Continuous, Pulsatile, and Failure", ASAIO Journal, vol. 51, No. 6, 2005, pp. 711-718.
Voigt et al., "Suction Detection for the Micromed Debakey Left Ventricular Assist Device", ASAIO Journal, vol. 51, No. 4, 2005, pp. 321-328.
Vollkron et al., "Development of a Reliable Automatic Speed Control System for Rotary Blood Pumps", The Journal of Heart and Lung Transplantation, vol. 24, No. 11, Nov. 2005, pp. 1878-1885.
Vollkron et al., "Development of a Suction Detection System for Axial Blood Pumps", Artif Organs, vol. 28, No. 8, 2004, pp. 709-716.

\* cited by examiner

GENERATING ARTIFICIAL PULSE

CROSS-REFERENCE TO RELATED APPLICATIONS

The present application is a Continuation of U.S. application Ser. No. 16/055,471 filed Aug. 6, 2018 (Allowed); which is a Continuation of U.S. application Ser. No. 15/785,097 filed Oct. 16, 2017 (now U.S. Pat. No. 10,086,122); which is a Continuation of U.S. patent application Ser. No. 15/221,456 filed Jul. 27, 2016 (now U.S. Pat. No. 9,801,988); which is a Continuation of U.S. patent application Ser. No. 14/592,630 filed Jan. 8, 2015 (now U.S. Pat. No. 9,433,717); which is a Continuation of U.S. patent application Ser. No. 14/261,817 filed Apr. 25, 2014 (now U.S. Pat. No. 8,961,388); which is a Continuation of U.S. application Ser. No. 13/926,044 filed Jun. 25, 2013 (now U.S. Pat. No. 9,011,312); which is a Divisional of U.S. patent application Ser. No. 13/241,831 filed Sep. 23, 2011 (now U.S. Pat. No. 8,506,471); which claims the benefit of U.S. Provisional Appln No. 61/386,018 filed Sep. 24, 2010; the disclosures of which are incorporated herein by reference in their entirety for all purposes.

FIELD

This description relates to generating an artificial pulse.

BACKGROUND

Ventricular assist devices, known as VADs, are types of blood pumps used for both short-term and long-term applications where a patient's heart is incapable of providing adequate circulation. For example, a patient suffering from heart failure may use a VAD while the patient awaits a heart transplant. In another example, a patient may use a VAD while the patient recovers from heart surgery. Thus, a VAD can supplement a weak heart or can effectively replace the natural heart's function. VADs can be implanted in the patient's body and powered by an electrical power source outside the patient's body.

BRIEF SUMMARY

In one general aspect, a continuous flow blood pump can be operated to provide pulsatile blood flow. The motor speed for the pump can be modulated in a repeating cycle that includes a sequence of two or more speed levels. Operation of the pump can produce pressure changes that imitate a rate of pressure change of a natural physiologic pulse.

In another general aspect, pumping blood in a pulsatile manner includes operating a blood pump at a first speed for a first period of time, reducing the speed of the blood pump from the first speed to a second speed, operating the blood pump at the second speed for a second period of time, reducing the speed of the blood pump from the second speed to a third speed, operating the blood pump at the third speed for a third period of time, and increasing the speed of the blood pump from the third speed to the first speed.

Implementations can include one or more of the following features. For example, increasing the speed of the blood pump from the third speed to the first speed includes increasing the speed of the blood pump from the third speed to a fourth speed, operating the blood pump at the fourth speed for a fourth period of time, and increasing the speed of the blood pump from the fourth speed to the first speed. The second period of time is longer than a sum of the first period of time and the third period of time. Operating the blood pump at the first speed, reducing the speed of the blood pump from the first speed to the second speed, operating the blood pump at the second speed, reducing the speed of the blood pump from the second speed to the third speed, operating the blood pump at the third speed, and increasing the speed of the blood pump from the third speed to the first speed comprise a cycle, and pumping blood in a pulsatile manner further includes repeating the cycle. The duration of the second period of time is greater than half of the duration of the cycle. Operating the blood pump at the second speed for the second period of time includes operating the blood pump to produce a blood flow rate that has a predetermined relationship relative to an average blood flow rate for the cycle. Operating the blood pump at the second speed for the second period of time includes operating the blood pump to produce a blood flow substantially the same as the average blood flow rate for the cycle.

One or more of reducing the speed of the blood pump from the first speed to a second speed, reducing the speed of the blood pump from the second speed to a third speed, and increasing the speed of the blood pump from the third speed to the first speed includes one or more of a step-wise reduction in speed and a curvilinear reduction in speed. Operating the blood pump at the second speed includes operating the blood pump at the second speed during at least a portion of a contraction of a ventricle of human heart that is in blood flow communication with the blood pump. Pumping blood in a pulsatile manner also includes determining, based on a relationship between a speed of the blood pump and a power consumption of the blood pump, a synchronization between operating the impeller at the second speed and contraction of a ventricle of a human heart that is in blood flow communication with the blood pump. A generated pulsatile blood flow includes a temporal rate of change of blood pressure that approximates a temporal rate of change of blood pressure of a physiologic pulse. One or more of reducing the speed of the blood pump from the first speed to a second speed, reducing the speed of the blood pump from the second speed to a third speed, and increasing the speed of the blood pump from the third speed to the first speed includes generating a drive signal at a first time to produce a corresponding change in operating speed at a desired time. The second period of time is greater than the first period of time.

In another general aspect, a blood pump controller includes a waveform generator to generate a waveform for operating a blood pump, and a drive waveform transmitter to supply the generated drive waveform to the blood pump. The generated waveform is configured to operate a blood pump at a first speed for a first period of time, reduce the speed of the blood pump from the first speed to a second speed, operate the blood pump at the second speed for a second period of time, reduce the speed of the blood pump from the second speed to a third speed, operate the blood pump at the third speed for a third period of time, and increase the speed of the blood pump from the third speed to the first speed.

Implementations can include one or more of the following features. For example, increasing the speed of the blood pump from the third speed to the first speed includes increasing the speed of the blood pump from the third speed to a fourth speed, operating the blood pump at the fourth speed for a fourth period of time, and increasing the speed of the blood pump from the fourth speed to the first speed. The second period of time is longer than a sum of the first period of time and the third period of time. Operating the blood pump at the first speed, reducing the speed of the blood pump from the first speed to the second speed, operating the blood pump at the second speed, reducing the speed of the blood pump from the second speed to the third speed, operating the blood pump at the third speed, and increasing the speed of the blood pump from the third speed to the first speed comprise a cycle, and wherein the generated waveform is configured to repeat the cycle. The duration of the second period of time is greater than half of the duration of the cycle. Operating the blood pump at the second speed for the second period of time includes operating the blood pump to produce a blood flow rate that has a predetermined relationship relative to an average blood flow rate for the cycle. Operating the blood pump at the second speed for the second period of time includes operating the blood pump to produce a blood flow substantially the same as the average blood flow rate for the cycle.

The generated waveform is configured to change the speed of the blood pump via one or more of a step-wise change in speed and a curvilinear change in speed. The generated waveform operates the blood pump at the second speed during a contraction of a ventricle of a human heart that is in blood flow communication with the blood pump. The blood pump controller further includes a processor configured to determine, based on a relationship between a speed of the blood pump and a power consumption of the blood pump, a synchronization between operating the blood pump at the second speed and a contraction of a ventricle of a human heart that is in blood flow communication with the blood pump. The generated waveform drives the blood pump to generate a temporal rate of change of blood pressure that approximates a temporal rate of change of blood pressure of a physiologic pulse. The generated waveform is further configured to produce a corresponding change in pump operating speed at a desired time. The second period of time is greater than the first period of time.

In another general aspect, producing a pulsatile blood flow having a relatively low pressure portion and a relatively high pressure portion and having a rate of pressure change that mimics a rate of pressure change of a natural physiologic pulse includes operating a continuous flow blood pump to produce a first blood flow rate through the continuous flow blood pump associated with the relatively low pressure portion of the pulsatile blood flow, operating the continuous flow blood pump to produce a second blood flow rate through the continuous flow blood pump associated with the relatively high pressure portion of the pulsatile blood flow, and controlling the continuous flow blood pump to increase a blood flow rate through the continuous flow blood pump from the first flow rate to the second flow rate to produce the rate of pressure change that mimics the rate of pressure change of the natural physiologic pulse.

Implementations can include one or more of the following features. For example, operating the continuous blood flow pump to produce the second blood flow rate can include operating the continuous blood flow pump at a first operating speed, and controlling can include operating the continuous blood flow pump at a second operating speed, the second operating speed being associated with a third blood flow rate, the third blood flow rate being greater than the second blood flow rate. Operating the continuous flow blood pump to produce the second blood flow rate includes operating the continuous flow blood pump to produce the second blood flow rate such that the relatively high pressure portion has a duration that is longer than a duration of the relatively low pressure portion. Repeating a cycle in which the duration of the relatively high pressure portion is greater than half of the duration of the cycle. The cycle includes operating the continuous flow blood pump to produce the first blood flow rate, operating the continuous flow blood pump to produce the second blood flow rate, and controlling the continuous flow blood pump to increase the blood flow rate. Operating the continuous flow blood pump to produce the second blood flow rate includes operating the continuous flow blood pump to produce the second blood flow rate such that the second blood flow rate has a predefined relationship with an average blood flow rate of the pulsatile blood flow. The second blood flow rate is substantially equal to an average blood flow rate of the pulsatile blood flow. Controlling the continuous flow blood pump to increase the blood flow rate includes controlling the continuous flow blood pump to increase the blood flow rate through the continuous flow blood pump from the first flow rate to the second flow rate such that the blood flow rate through the continuous flow blood pump overshoots the second flow rate to produce the rate of pressure change that mimics the rate of pressure change of the natural physiologic pulse.

The details of one or more implementations are set forth in the accompanying drawings and the description below. Other features will be apparent from the description and drawings, and from the claims.

DETAILED DESCRIPTION

Figure 1:
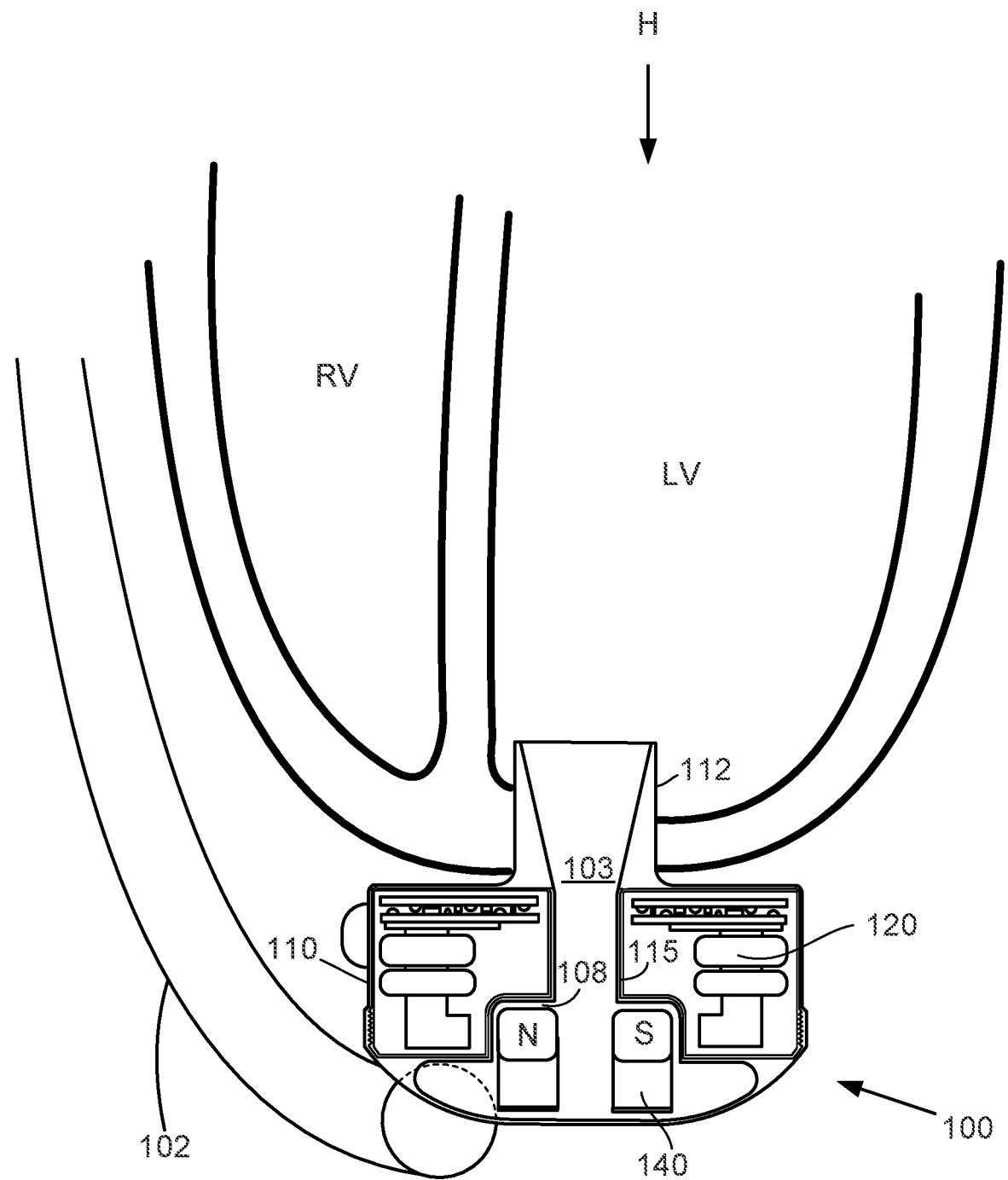
FIG. 1 is a diagram of an implanted blood pump.

With reference to FIG. 1, a left ventricular assist blood pump 100 is implanted in a patient's body to assist or replace the patient's heart H in pumping blood. Pump 100 has a housing 110 including an inlet cannula 112 that extends into the left ventricle LV of the heart H. Connected to the housing 110 is an outlet conduit 102 that conducts blood from the blood pump 100 to the patient's circulatory system. The blood pump 100 can be a continuous flow pump, for example, a rotary pump. The blood pump 100 can provide axial flow, centrifugal flow, or mixed axial and centrifugal flow.

The blood pump 100 includes a stator 120 and a rotor 140. The rotor 140 includes an impeller to move blood from the inlet cannula 112 to the outlet conduit 102. For example, the blood pump 100 can be the pump described in U.S. Provisional Patent Application Ser. No. 61/375,504, filed Aug. 20, 2010, the entire contents of which are hereby incorporated by reference. In some implementations, the rotor 140 is separated from an internal wall 115 of the housing 110 by a gap 108. In use, the gap is from approximately 0.1 millimeters to approximately 2.0 millimeters. For example, in some implementations, the gap 108 is approximately 0.5 millimeters during use. Additionally, in some implementations, the rotor has a weight from approximately 5 grams to approximately 50 grams. For example, in some implementations, the rotor 140 has a weight of approximately 10 grams.

The rotation speed of the rotor 140 can be controlled to produce a desired blood flow rate. The desired blood flow rate can be selected to provide a desired level of assistance to the patient's heart H. For example, the blood flow rate can be selected to partially assist the blood circulation function of the patient's heart H. Alternatively, the blood flow rate can be selected to substantially replace the blood circulation function of the patient's heart. The rate of flow of blood from the inlet cannula 112 to the outlet conduit 102 is controlled, at least in part, by controlling the rate of rotation of the rotor 140 based on a direct relationship between the pump speed and the rate of blood flow through the blood pump 100.

With reference to FIGS. 1 and 4-11, the left ventricular assist blood pump 100 has a puck-shaped housing 110 and is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2, 4, and 6-9, for example.

Figure 2:
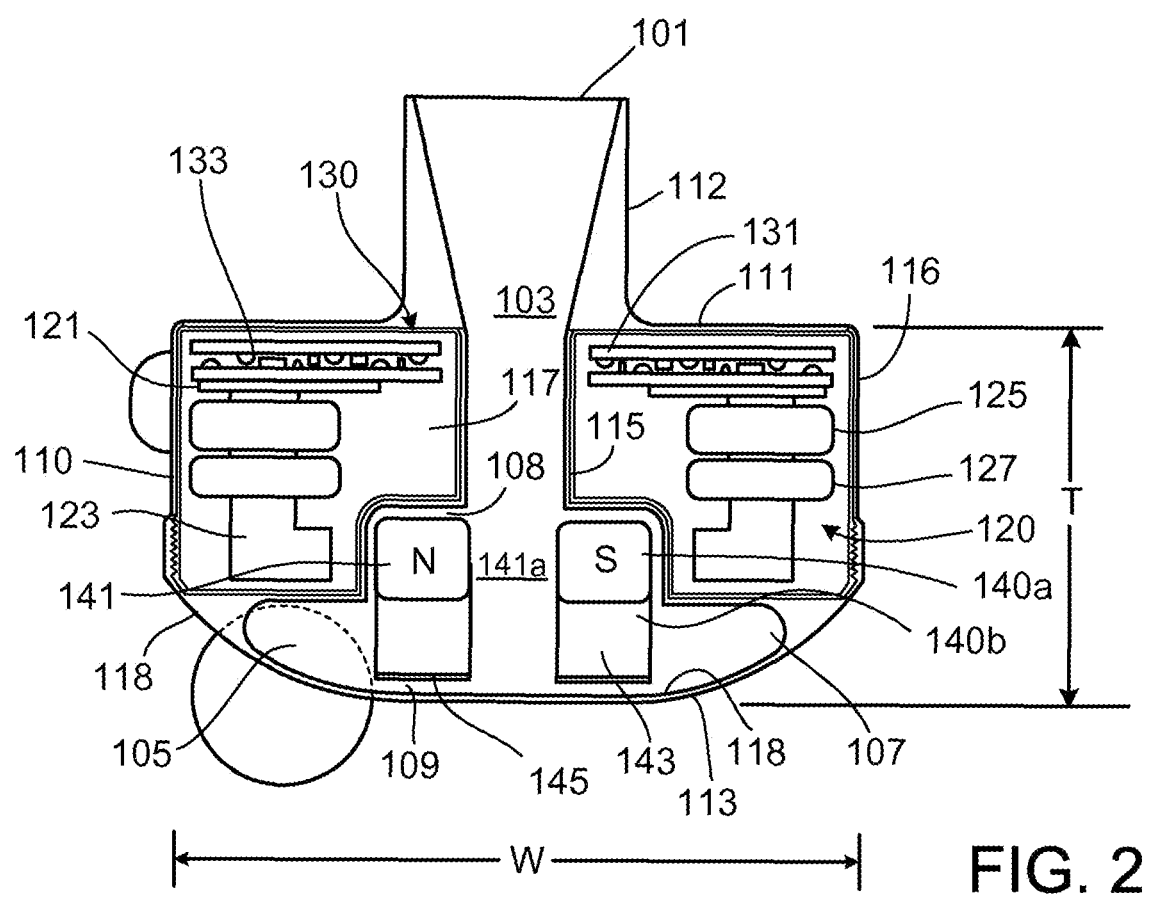
FIG. 2 is a cross-sectional view of the blood pump of FIG. 1.

Referring to FIG. 2, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadably engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components 133 carried on the circuit boards 131 to control the operation of the pump 100 by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

Figure 3:
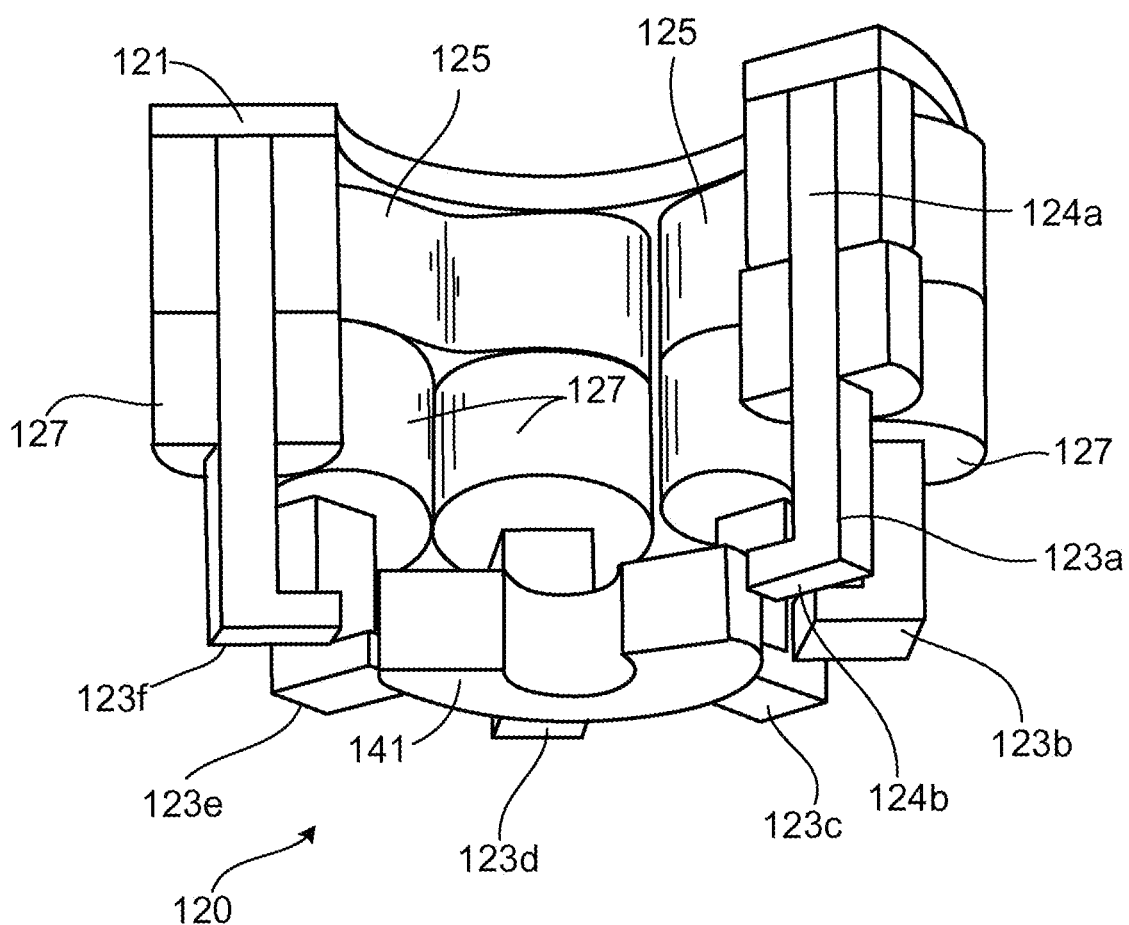
FIG. 3 is a partial cut-away perspective view of a stator of a blood pump.
Figure 4:
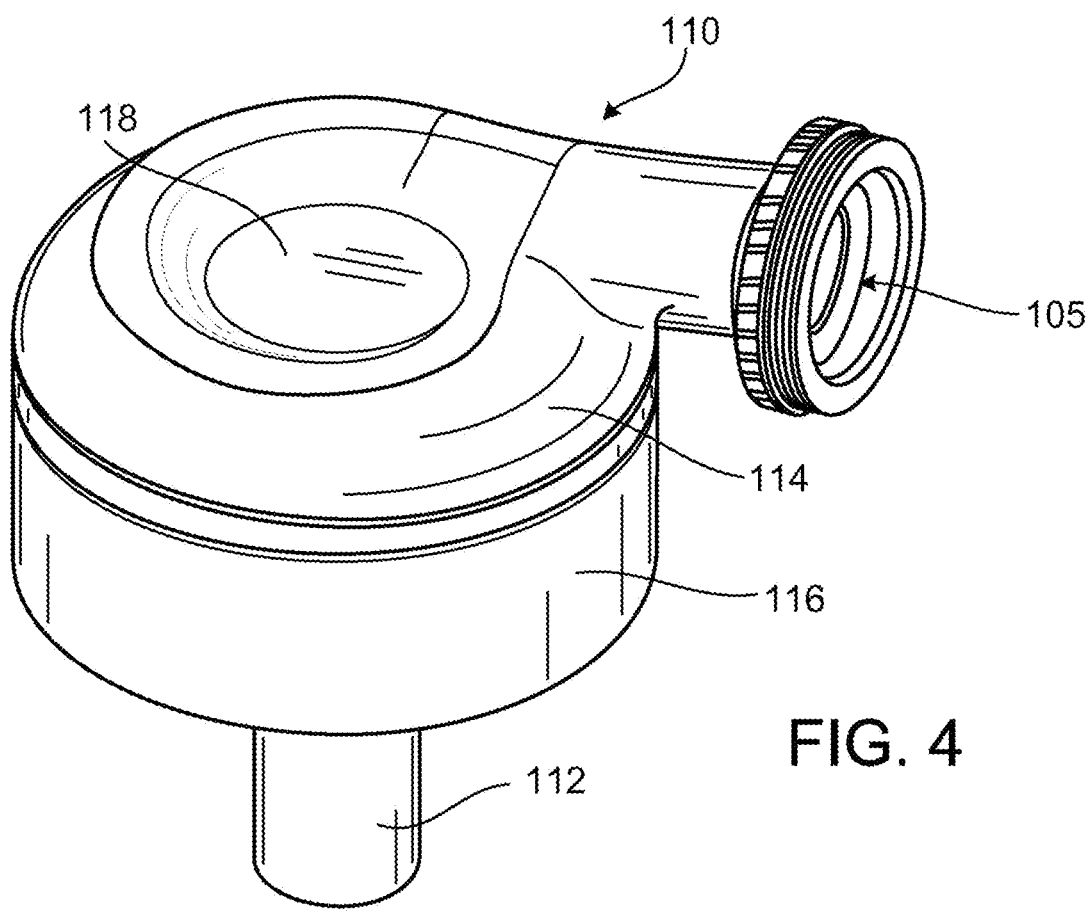
FIG. 4 is a bottom perspective view of a blood pump.
Figure 5:
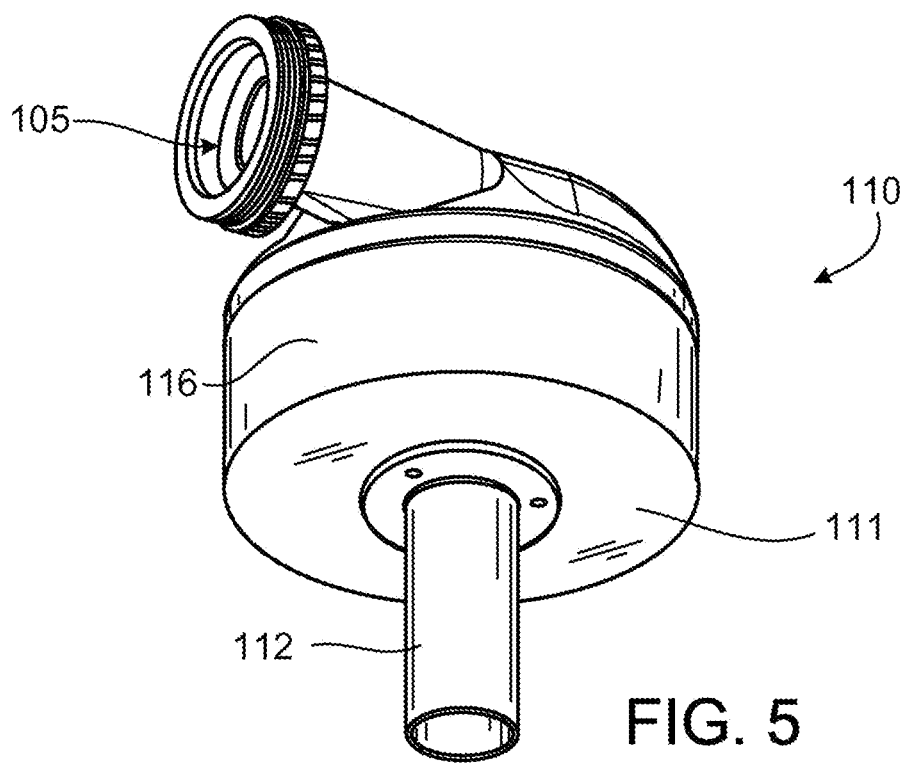
FIG. 5 is a top perspective view of the blood pump of FIG. 4.
Figure 6:
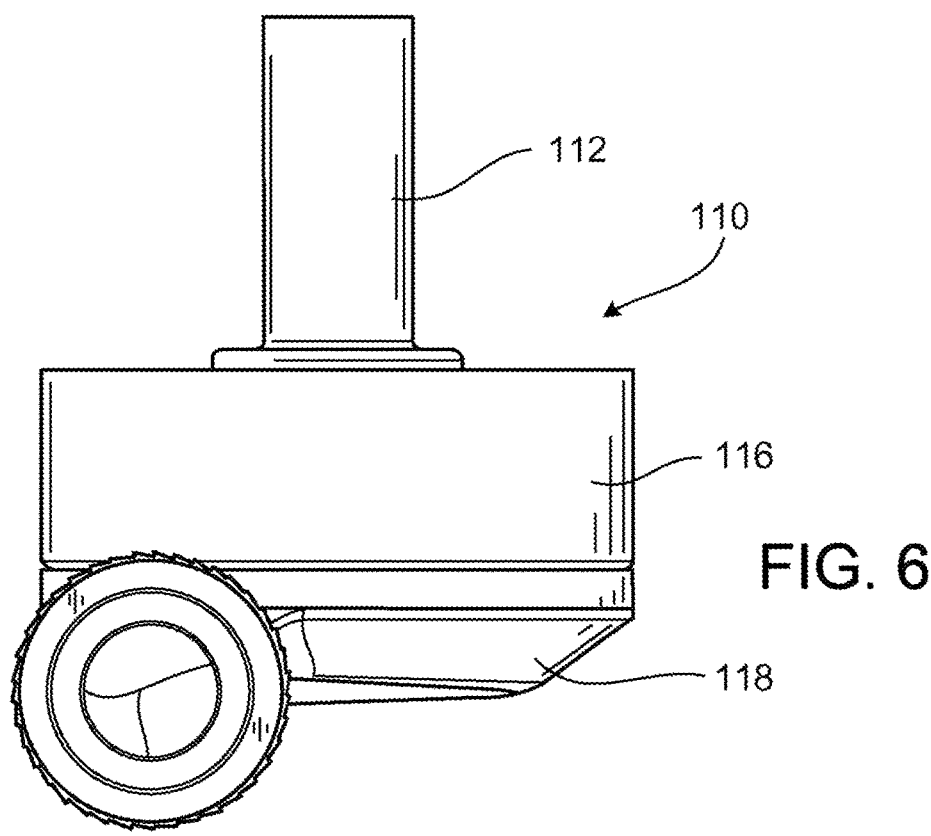
FIG. 6 is a front view of the blood pump of FIG. 4.
Figure 7:
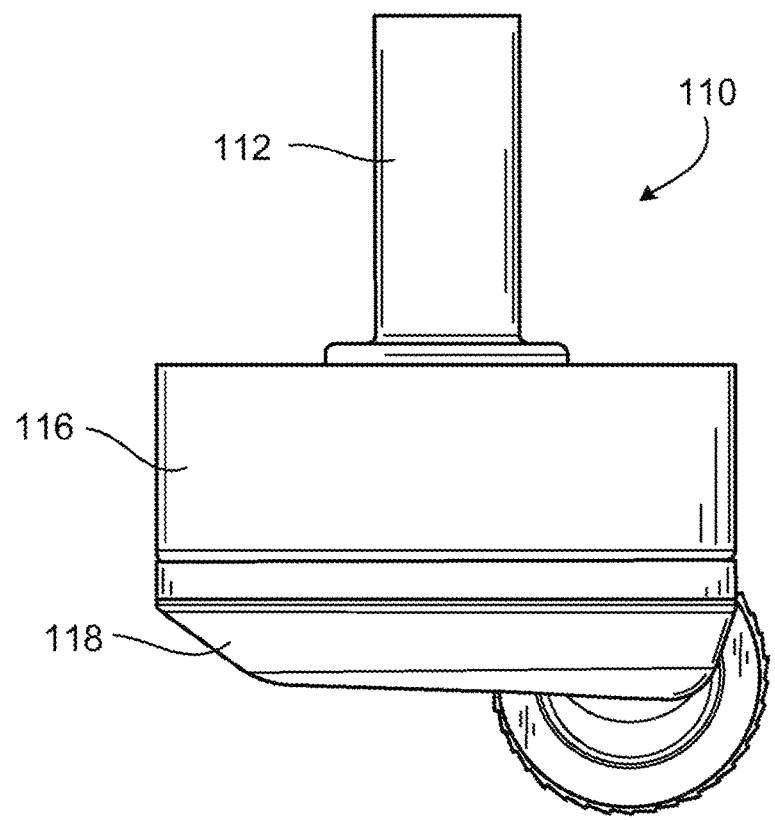
FIG. 7 is a back view of the blood pump of FIG. 4.
Figure 8:
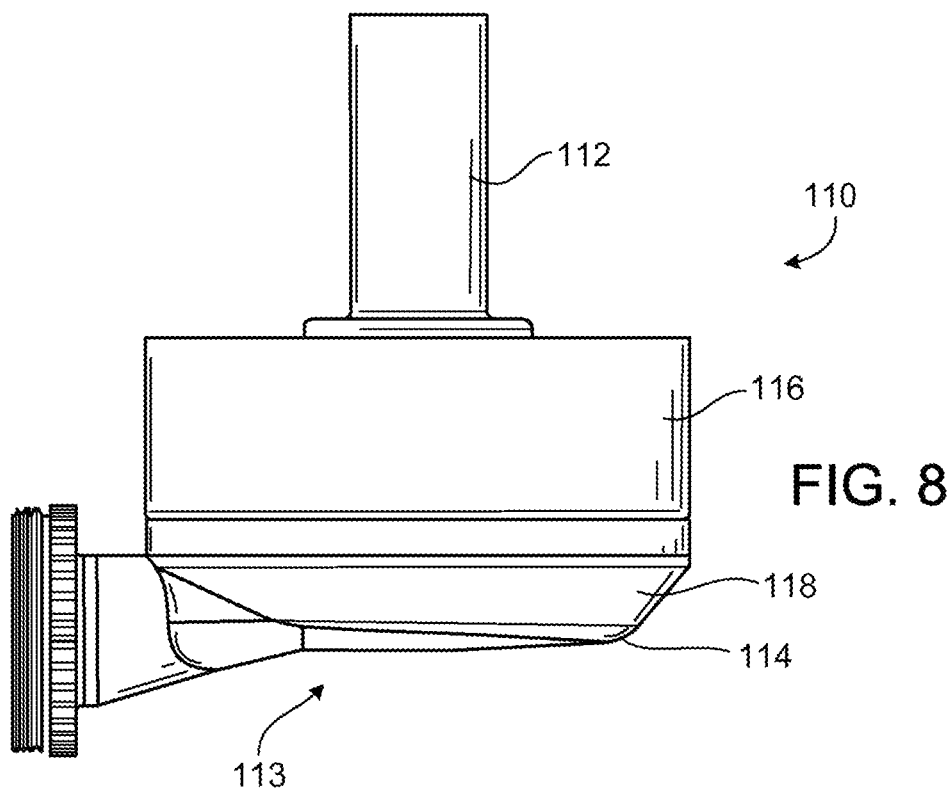
FIG. 8 is a right side view of the blood pump of FIG. 4.
Figure 9:
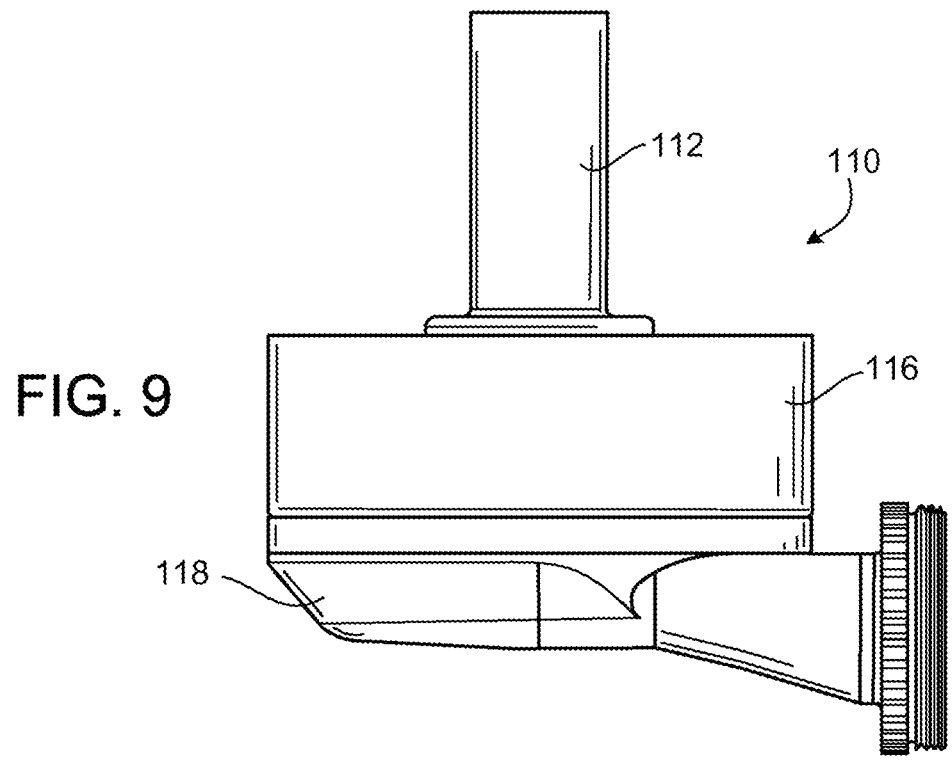
FIG. 9 is a left side view of the blood pump of FIG. 4.
Figure 10:
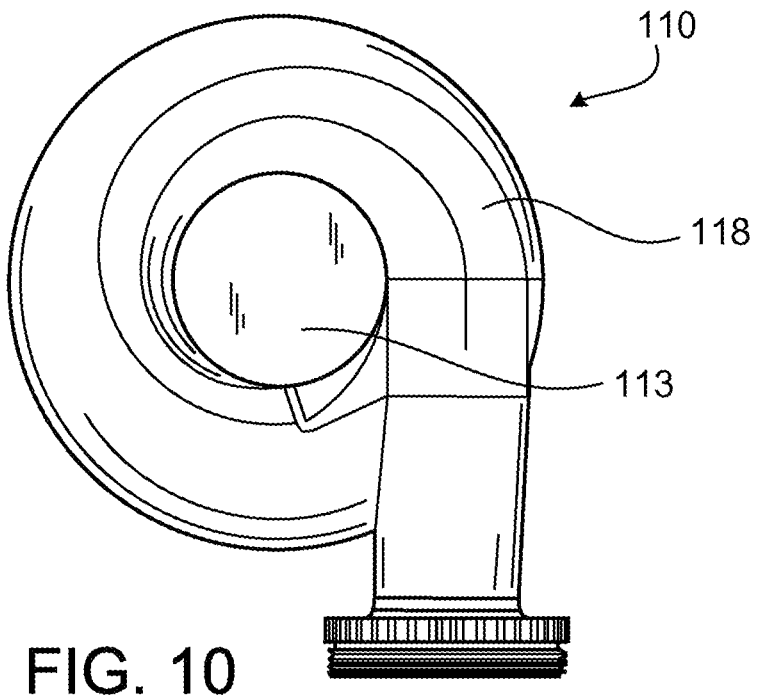
FIG. 10 is a bottom view of the blood pump of FIG. 4.
Figure 11:
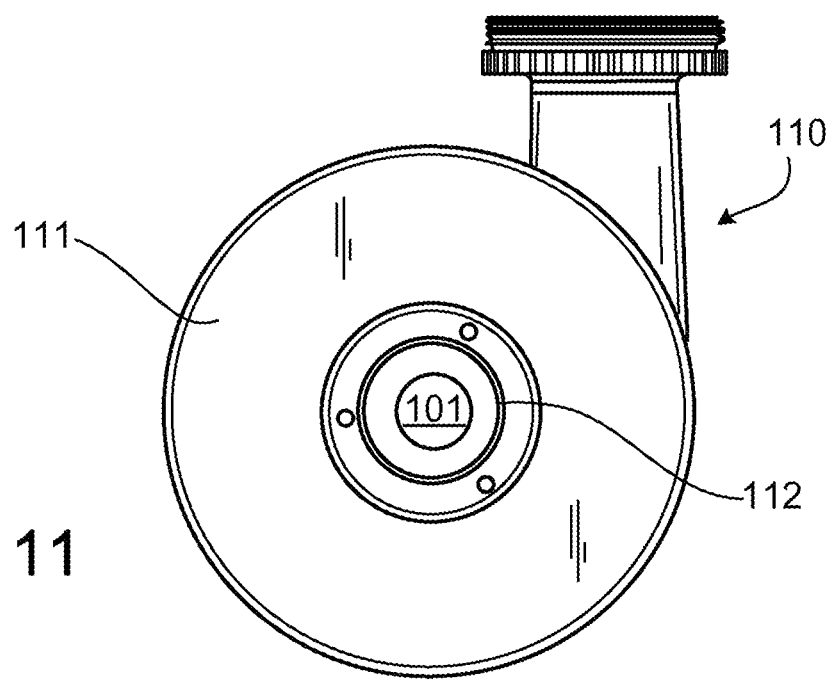
FIG. 11 is a top view of the blood pump of FIG. 4.

With continued reference to FIG. 2 and with reference to FIG. 3, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a also has a second leg 124b that extends from the first leg 124a towards the dividing wall 115 proximate the location of the permanent magnet 141 of the rotor 140. Each of the pole pieces 123a-123f also has a levitation coil 127 for generating an electromagnetic field to control the radial position of the rotor 140.

Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference. The control electronics 130 and the stator 120 receive electrical power from a remote power supply via a cable 119 (FIG. 1).

The rotor 140 is arranged within the housing 110 such that its permanent magnet 141 is located upstream of impeller blades in a location closer to the inlet opening 100. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 141 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105.

A number of implementations have been described. Nevertheless, it will be understood that various modifications may be made without departing from the spirit and scope of the claimed invention. For example, the cap 118 can be engaged with the peripheral wall 116 using a different attachment mechanism or technique, including snap-fit engagement, adhesives, or welding. Additionally, while the cap 118 has been described as defining the outlet opening 105 and the chamfered edge 114, the outlet opening 105 and/or the chamfered edge 114 can be defined by the peripheral wall 116 or by both the peripheral wall 116 and the cap 118. Similarly, the dividing wall 115 can be formed as part of the cap 118.

Additionally, the rotor 140 can include two or more permanent magnets. The number and configuration of the pole pieces 123 can also be varied. The operation of the control electronics 130 is selected to account for the number and position of pole pieces of the stator and permanent magnets of the rotor. Also, the cap 118 can be engaged with the peripheral wall using other techniques, such as adhesives, welding, snap-fit, shrink-fit, or other technique or structure. Similarly, the first face 111 may be formed from a separate piece of material than the peripheral wall 116 and the first face 111, including the inlet cannula 112, can be attached to the peripheral wall 116, such as by welding, after the control electronics 130 and the stator 120 have been mounted in the internal compartment 117. The shroud 145 may be omitted and optionally replaced by other flow control devices to achieve a desired pump efficiency. As another option, the control electronics 130 can be located external to the pump 100, such as in a separate housing implanted in the patient's abdomen, or external to the patient's body.

In some implementations, the dimensions of the housing 110 can be larger or smaller than those described above. Similarly, the ratio of the width W of the housing 110 to the thickness T of the housing can be different than the ratio described above. For example, the width W can be from about 1.1 to about 5 times greater than the thickness T. Additionally, the permanent magnet 141 of the rotor 140 can include two or more pairs of north and south magnetic poles. While the peripheral wall 116 and the dividing wall 115 are illustrated as cylinders having circular cross-sectional shapes, one or both can alternatively be formed having other cross-sectional shapes, such as oval, or an irregular shape. Similarly, the peripheral wall 116 can be tapered such that the housing does not have a constant width W from the first face 111 to the second face 113.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis, such as where the patient's aortic valve is surgically sealed.

In addition to producing blood flow at a desired rate, a pulsatile blood flow pattern may be desired. A pulsatile blood flow pattern includes time periods of relatively high blood flow rates and blood pressures and time periods of relatively low blood flow rates and blood pressures. Such a pulsatile blood flow pattern may be desired to augment or replace a weakened pulse in patients, especially those whose native cardiac output is small compared to the volume flow rate of the blood pump. Additionally, a pulsatile blood flow pattern may be desired to produce a physiologic response similar to that of a native pulsatile blood flow pattern and/or blood pulse pressure from a healthy heart. This physiologic response may be markedly different than the response of a blood pump operating at a constant speed. While non-pulsatile circulation can lead to certain physiologic, metabolic, and vasomotor changes, the clinical relevance of pulsatility for VADs is unclear. Nevertheless, it is hypothesized that pulsatile circulation may reduce blood stasis in the ventricles, help exercise the aortic valve, improve washing on the distal side of atherosclerotic lesions, increase coronary and/or end organ perfusion, reduce the risk of ventricular suction, reduce the propensity for maladies related to reduced pulsatility, such as arteriovenous malformations, and increase myocardial recovery. Further, it is expected that these phenomena do not require mimicking a native pulse waveform in its entirety. Rather, such may be accomplished with the techniques and waveforms described herein.

Importantly, various characteristics of the artificial pulse may differ substantially from those of a physiologic pulse even while producing a response in the body that is similar to that caused by the physiologic pulse. Although with the multitude of potential clinical advantages there may be different aspects of a native pulse that mediate physiologic response, it is generally understood that the dominant source of dissipated energy that characterizes a meaningful pulse is the pressure wave generated at the start of cardiac systole. Accordingly, the artificial pulse described herein can include a relatively brief perturbation of a nature designed to produce such dissipated energy.

In some implementations, an artificial pulse cycle includes a perturbation period that simulates the pulse pressure that occurs at the leading edge of systole of a physiologic pulse. The perturbation period can include, for example, a period during which the blood pump 100 is operated at a low speed, followed immediately by a period during which the blood pump 100 is operated at a higher speed. The artificial pulse cycle can also include a period longer than the perturbation period during which the pump 100 is operated at an intermediate speed, for example, a speed maintained between the speeds realized during the perturbation period.

Operating the pump at the intermediate speed can contribute to a high operating efficiency. The efficiency achieved can be greater than, for example, the efficiency of a pump that only alternates between equal periods of operation at a high speed and at a low speed. Typically, a continuous flow pump operates with highest efficiency near the middle of its rotational speed range. Therefore, it can be advantageous to operate such a pump at or near a mid-range speed for at least a portion of an artificial pulse cycle.

Some of the parameters that affect physiologic phenomena include pulse pressure and the rate of blood pressure change (dp/dt). For the blood pump 100, for example, pulse pressure and time variation in blood pressure are affected by the angular velocity of the rotor 140. Thus, the blood pump 100 can be selectively controlled to produce a pulsatile blood flow pattern, including a desired pulse pressure and/or a desired rate of pressure change, by producing a pump speed pattern that includes a time period of relatively high rotor rotation speeds and a time period of relatively low rotor rotation speeds. In some implementations, the pulse pressure produced by the blood pump 100 or produced by the blood pump 100 and the patient's heart H in combination can be approximately 10 mmHg or more, such as from approximately 20 mmHg to approximately 40 mmHg.

Figure 12:
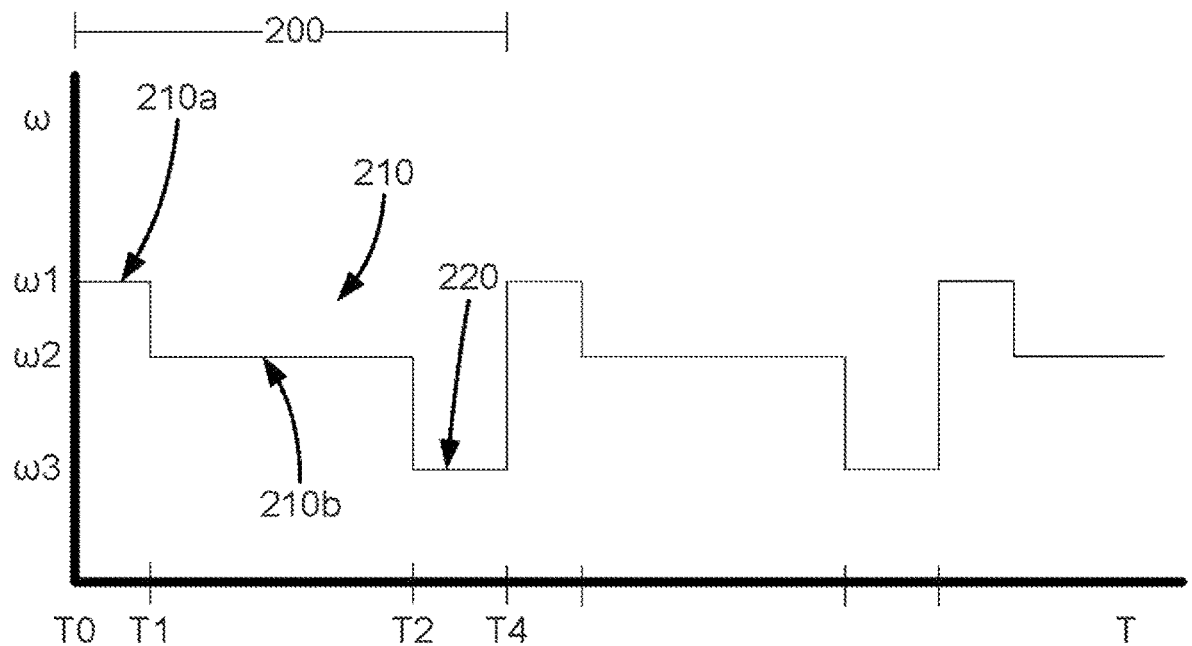
FIGS. 12-15 are diagrams illustrating pump speed patterns.

For example, the blood pump 100 can be operated to produce a pump speed pattern 200, illustrated in FIG. 12. The pump speed pattern 200 includes a first portion 210 with high pump speed producing a relatively high blood pressure, and a second portion 220 with low pump speed producing a relatively low blood pressure. Additionally, the pulsatile blood flow pattern can include a transition between the first portion 210 and the second portion 220 that produces a desired rate of pressure change in the patient's circulatory system, such as a rate of pressure change that simulates a natural physiologic pulse and that produces desired physiological effects associated with rate of pressure change. In some implementations, the rate of pressure change produced by the transition is, for example, between 500 to 1000 mmHg per second.

The first portion 210 and/or the second portion 220 of the pump speed pattern 200 can include multiple segments. In some implementations, the segments each have predetermined durations. As also shown in FIG. 12, the first high speed portion 210 of the pump speed pattern 200 includes a first segment 210a and a second segment 210b. In the first segment 210a, the rotor 140 is rotated at a first rotation speed $\omega 1$ for a first period of time from a time T0 to a time T1. At the time T1, the rotation speed of the rotor 140 is rapidly decreased from the first rotation speed $\omega 1$ to a second rotation speed $\omega 2$, producing a stepped transition. The rotor 140 is rotated at the second rotation speed $\omega 2$ for a second period of time from the time T1 to a time T2 during a second segment 210b of the first portion 210 of the pump speed pattern 200. At the time T2, the rotation speed of the rotor 140 is decreased to a third rotation speed $\omega 3$ for a third period of time from the time T2 to a time T4 during the second portion 220 of the pump speed pattern 200. This speed decrease may be as rapid as the aforementioned speed increase, or more gradual to mimic pressure changes during native diastole.

In the pump speed pattern 200, the second rotation speed $\omega 2$ is a target high blood flow pump speed, and the first rotation speed $\omega 1$ is a desired overshoot pump speed that is selected to increase the rate of change of the blood pressure during the first period. The first period of time from the time T0 to the time T1, during which the blood pump 100 is operated at the first rotation speed $\omega 1$, is shorter than the second period of time from the time T1 to the time T2, during which the blood pump 100 is operated at the second rotation speed $\omega 2$. The first period of time can be from approximately 0.01 seconds to approximately 1 second. In some implementations, the first period of time is approximately 0.05 seconds in duration. In some implementations, the first period of time can be approximately equal to, or greater than the second period of time.

Additionally, the duration of the first period can be selected to produce a desired pulse pressure, i.e., the difference between blood pressure before the speed change time T1 and during the time T1, and can be selected independently of the duration of the second period of time. The first portion 210, including the first and second time periods from the time T0 to the time T2, is longer than the second portion 220. In some implementations, the first and second time periods from the time T0 to the time T2 can be shorter than, longer than, or substantially the same duration as the second portion 220. For example, to increase the duration of pumping at the higher flow rate relative to pumping at the lower rate while still benefiting from the occasional pulse, it may be advantageous for the first portion 210 to be longer than the second portion 220. If desired, the speed of the blood pump 100 is increased to the first rotation speed $\omega 1$ and the pump speed pattern 200 can be repeated. The pump speed pattern 200 can be repeated on a continuous or discontinuous basis, and the increase of rotation speed of the rotor 140 is also sufficiently rapid to produce a desired rate of pressure change.

The concept of overshooting the rotation speed $\omega 2$ with a greater speed, such as rotation speed $\omega 1$, is based upon partly decoupling pulse pressure, i.e. the difference between the blood pressures before and after the speed change, from the volume flow rate at the higher speed. Thus, target pulse pressures and volume flow rates can be attained at various flow conditions. Ideal values will vary with particular pump design and requirements.

As shown in FIG. 12, the period 210b can be longer than the period 210a. The period 210b can also be longer than the portion 220. In some implementations, the duration of the period 210b is more than half of the duration of the pump speed pattern 200. For example, the duration of the period 210b can be 60%, 70%, 80% or more of the duration of the pump speed pattern 200. As an alternative, depending on patient needs and pump characteristics, the duration of the period 210b can be 50% or less of the duration of the pump speed pattern 200, for example, 40%, 30%, 20% or less.

Operating the pump at the rotation speed $\omega 2$ during the period 210b can contribute to a high hydraulic efficiency during the pump speed pattern 200. During the pump speed pattern 200, the pulse pressure generated in a patient's body is generally correlated to the change in pump rotation speed, for example, the magnitude of the speed change between the speeds $\omega 3$ and $\omega 1$ at time T4. Therefore, to simulate a pressure change that occurs at the beginning of systole of a physiologic pulse, a significant speed differential between the rotation speeds $\omega 3$ and $\omega 1$ is generally desired. The speed differential can be, for example, 1000 rpm, 2000 rpm, or more depending on the characteristics of the blood pump 100. Due to the magnitude of the speed differential, one or both of the speeds $\omega 3$ to $\omega 1$ may occur outside the range of highest operating efficiency of the blood pump 100.

The rotation speed $\omega 2$ can be a speed that results in a high hydraulic efficiency of the blood pump 100, for example, a speed near the middle of the operating range of the blood pump 100. During the pump speed pattern 200, the blood pump 100 can operate at the speed $\omega 2$ that results in high efficiency for a significant portion of the pump speed pattern 200, contributing to a high efficiency. As described above, the blood pump 100 can operate at the speed $\omega 2$ for more than half of the duration at the pump speed pattern 200. Thus the blood pump 100 can operate in a highly efficient manner for the majority of the pump speed pattern 200 and can also produce a pressure change that simulates the beginning of systole of a physiologic heart. Accordingly, some implementations of the pump speed pattern 200 can provide a higher efficiency than control modes that attempt to mimic all aspects of a native cardiac cycle.

The length of the period 210b relative to the length of the pump speed pattern 200 can vary based on the frequency of the artificial pulse. The duration of the period 210a and of the portion 220, by contrast, can be independent of the pulse rate. To produce the desired physiological response, a minimum duration for the period 210a and the portion 220 can be selected, for example, 0.125 seconds. The period 210b can fill the remainder of the pump speed pattern 200.

As an example, the pump speed pattern 200 can have a duration of one second, for a frequency of 60 cycles per minute. Given that the period 210a and the portion 220 have a combined duration of 0.125 seconds, the period 210b can have a duration of 0.750 seconds, or 75% of the pump speed pattern 200. As another example, when the pump speed pattern 200 has a duration of two seconds (and thus a frequency of 30 cycles per minute), the duration of the period 210b can be 1.75 seconds, which is 87.5% of the duration of the pump speed pattern 200.

In some implementations, the rotation speed $\omega 2$ is selected such that the operation of the blood pump 100 at the rotation speed $\omega 2$ produces a flow rate that has a predetermined relationship relative to the average flow rate during the pump speed pattern 200. The flow rate during the portion 210b can be within a predefined range of the average flow rate, for example, within 30% or within 10% of the average flow rate. The flow rate during the portion 210b can be substantially equal to the average flow rate.

Selecting the rotation speed $\omega 2$ to produce a flow rate that is substantially equal to the average flow rate can facilitate a transition between a pulsatile control mode and another control mode, such as a continuous flow control mode. In some implementations, the blood pump 100 operates at a particular constant speed for the greater part of the pump speed pattern 200. Operation at the constant speed can occur during, for example, the period 210b. By adjusting the speeds $\omega 1$ and $\omega 3$ and duration of the period 210a and of the portion 220, the average pump volume flow rate can be tuned to substantially match an average pump volume flow rate that would be realized in a different optional setting. Consequently, a clinician or patient can switch from an artificial pulse mode to another control mode in a manner that causes only a small difference or no difference in average volume flow rate. This can provide a clinical advantage when the artificial pulse is a selectable option among at least one alternative, for example, a constant speed option.

As an example, a speed set by a clinician for a constant speed mode can also be utilized for a constant speed portion of an artificial pulse mode. The speed can be selected by the clinician to produce a desired volume flow rate through the blood pump 100 during the constant speed mode (e.g., during continuous flow or non-pulsatile operation of the blood pump 100). In the artificial pulse mode, the same selected speed can be used as, for example, the rotation speed $\omega 2$ during the period 210b of the pump speed pattern 200. The speeds $\omega 1$, $\omega 3$ and the duration of the period 210a and the portion 220 are calculated or chosen to approximately balance the volume flow rate for the pump speed pattern 200. For example, the reduced flow rate during the portion 220 can offset the increased flow rate during the portion 210a. As a result, the net volume flow rate during the pump speed pattern 200 can substantially match the volume flow rate during the constant speed mode. Thus in either the constant speed mode or the artificial pulse mode, the volume flow rate can be approximately the same, permitting the clinician to switch from one mode to another without affecting the volume flow rate. This can help avoid potentially dangerous conditions that could occur if switching from one mode to another resulted in sudden changes in flow rate. For example, a sudden decrease in volume flow rate could cause acutely insufficient perfusion for the patient, and a sudden increase in volume flow rate could cause ventricular suction and arrhythmia.

Figure 13:
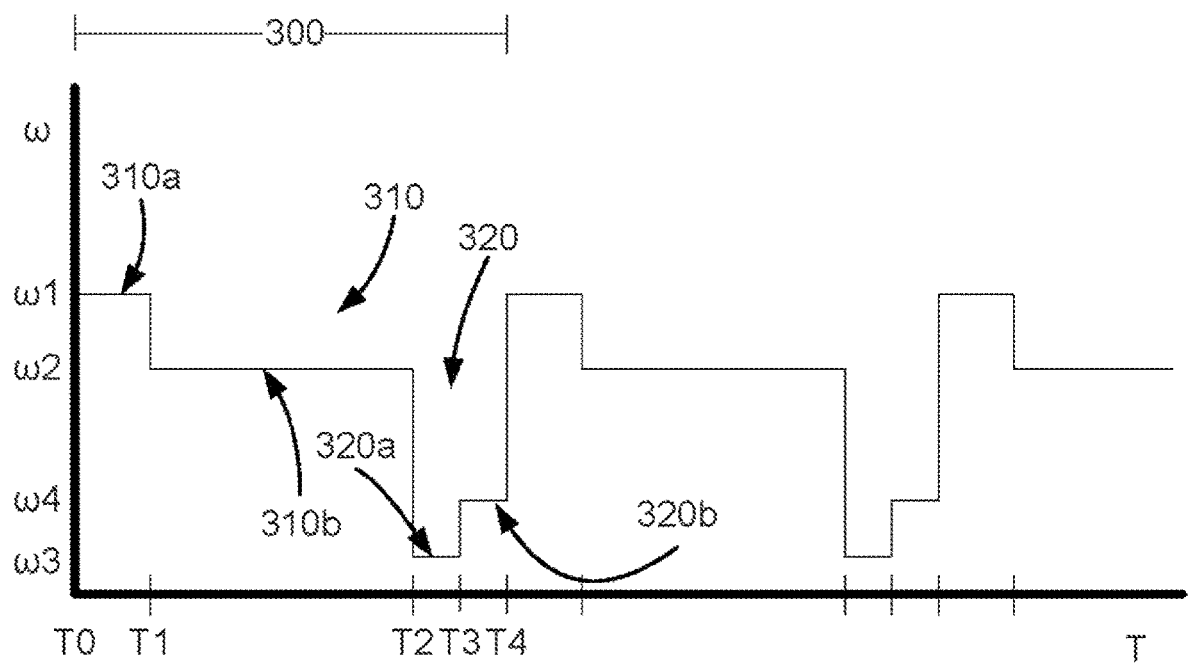

As mentioned above, the second portion 210 of the pump speed pattern 200 can also include multiple segments. For example, as shown in FIG. 13, a pump speed pattern 300 includes a first portion 310 that has a first segment 310a and a second segment 310b and the pump speed pattern 300 includes a second portion 320 that has a first segment 320a and a second segment 320b. During the first segment 310a, from the time T0 to the time T1, the blood pump 100 is operated at the first rotation speed $\omega 1$. At the time T1, the speed of the blood pump 100 is reduced to the second rotation speed $\omega 2$, and the blood pump 100 is operated at the second rotation speed $\omega 2$ for the second period of time from the time T1 to the time T2. At the time T2, the speed of the blood pump 100 is reduced from the second speed $\omega 2$ to the third rotation speed $\omega 3$. The blood pump 100 is operated at the third rotation speed $\omega 3$ for a third period of time from the time T2 to a time T3 during a first segment 320a of the second portion 320 of the pump speed pattern 300. At the time T3, the speed of the blood pump 100 is increased from the third rotation speed $\omega 3$ to a fourth rotation speed $\omega 4$, and the blood pump 100 is operated at the fourth rotation speed $\omega 4$ during a fourth period of time from the time T3 to the time T4 during a second segment 320b of the second portion 320 of the pump speed pattern 300. If desired, the speed of the blood pump 100 is increased to the first rotation speed $\omega 1$ and the pump speed pattern 300 can be repeated. The pump speed pattern 300 can be repeated on a continuous or discontinuous basis, and the increase of rotation speed of the rotor 140 is also sufficiently rapid to produce a desired rate of pressure change.

Similar to the concept of overshooting $\omega 2$ in pattern 200, the concept of overshooting the rotation speed $\omega 4$ with a lower rotation speed, such as the rotation speed $\omega 3$, is also based upon decoupling pulse pressure from the volume flow rate at the lower rotation speed $\omega 4$. Thus, the pump speed pattern 300 more completely decouples target pulse pressures and volume flow rates than the pump speed pattern 200, and ideal values can be attained, or more closely approximated, at various flow conditions.

Figure 14:
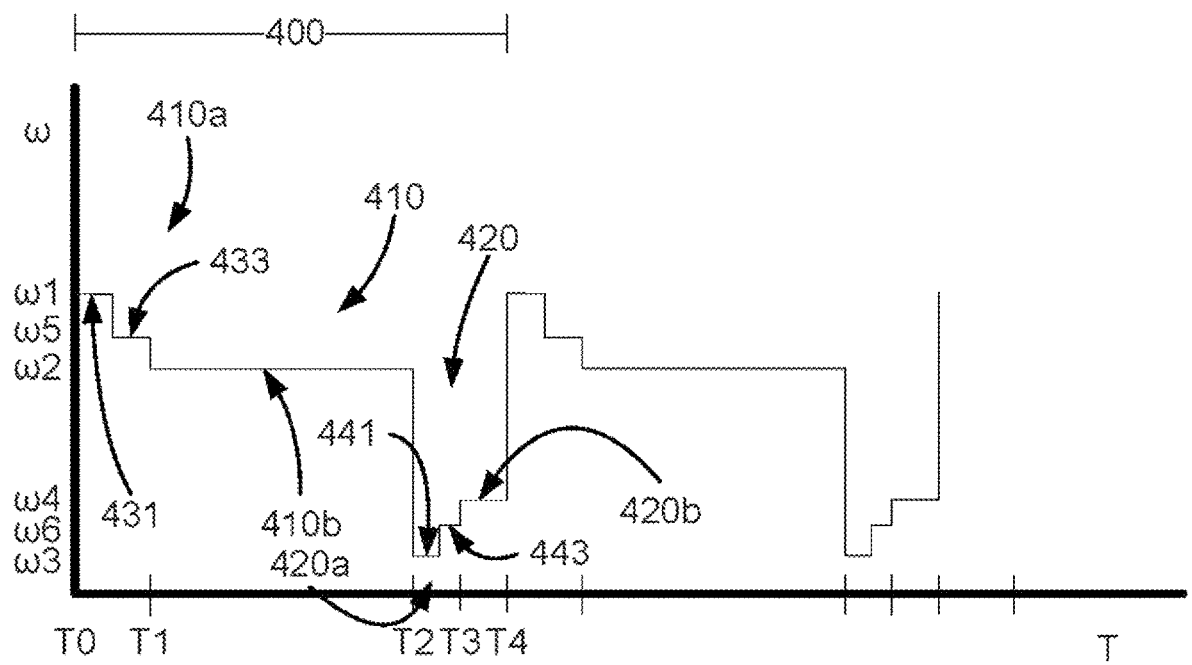

While a single overshoot pump speed for a transition between pump speeds are illustrated and described with reference to FIGS. 12 and 13, multiple overshoot pump speeds for one or more transitions can be used. For example, FIG. 14 illustrates a pump speed pattern 400 that includes multiple overshoot pump speeds for each transition. The pump speed pattern 400 includes a first portion 410 having a first segment 410a and a second segment 410b, and that includes a second portion 420 having a first segment 420a and a second segment 420b. The first segment 410a of the first portion 410 of the pump speed pattern 400 includes a first step 431 during which the blood pump 100 is operated at the first rotation speed $\omega 1$ to overshoot the target pump speed $\omega 2$ and a second transition step 433 during which time the blood pump 100 is operated at a fifth speed $\omega 5$ to transition from the first rotation speed $\omega 1$ to the second rotation speed $\omega 2$. Similarly, the first segment 420a of the second portion 420 includes a first step 441 during which the blood pump 100 is operated at the third rotation speed $\omega 3$ and a second segment 443 during which the blood pump 100 is operated at a sixth speed $\omega 6$ to transition between the third speed $\omega 3$ and the fourth rotation speed $\omega 4$. If desired, the speed of the blood pump 100 is increased to the first rotation speed $\omega 1$ and the pump speed pattern 400 can be repeated. The pump speed pattern 400 can be repeated on a continuous or discontinuous basis, and the increase of rotation speed of the rotor 140 is also sufficiently rapid to produce a desired rate of pressure change.

The concept of creating multiple stepwise rotation speed changes is based upon producing the physiologic response that is similar to that produced during human cardiac systole and diastole. This is distinct from mimicking the nature of a native pulse waveform in its entirety. As described above, greater hydraulic efficiency can often be achieved by avoiding imitation of the physiologic pressure waveform over the pulse cycle. It was previously mentioned that an artificial pulse offers a multitude of potential clinical advantages. For some or all of these potential clinical advantages, the benefit of closely matching the energy dissipated during a healthy native pulse varies. To the extent that close matching facilitates achieving these potential clinical advantages, the additional complexity of pattern 400 may be warranted.

Figure 15:
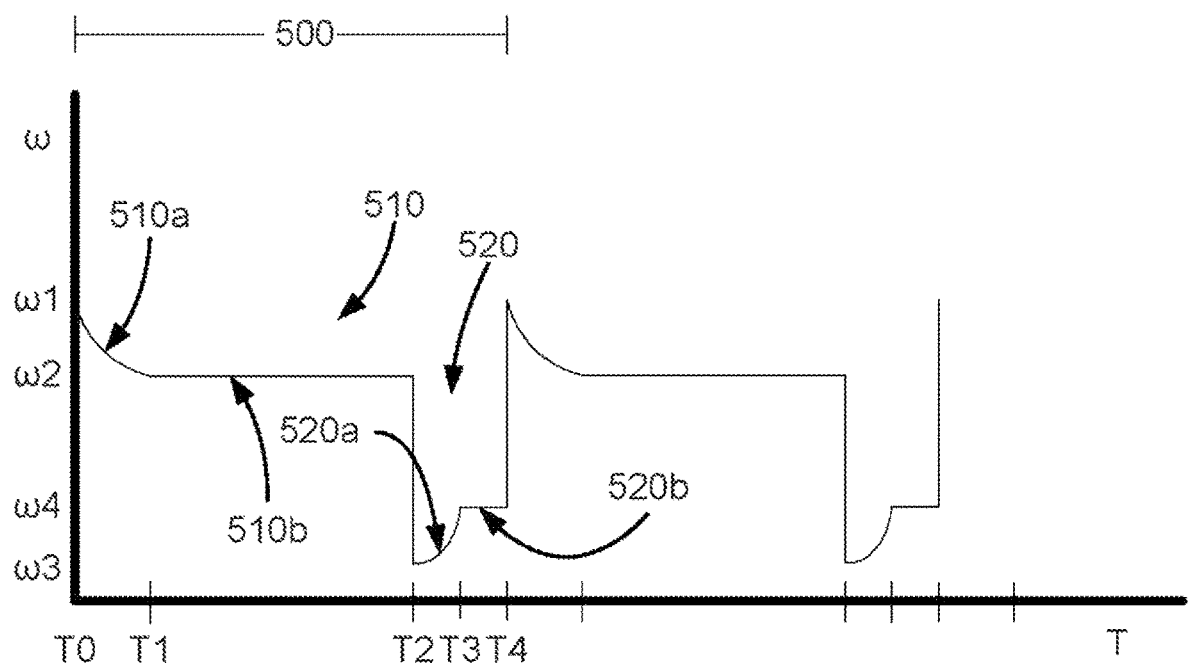

In contrast to the stepped or discontinuous transitions discussed above with respect to FIGS. 12-14, smooth or continuous transitions may be used in place of, or in combination with, stepped transitions between different pump operation speeds. For example, smooth transitions are illustrated in the pump speed pattern 500 of FIG. 15. The pump speed pattern 500 includes a first portion 510 and a second portion 520. The first portion 510 includes a first segment 510a during which the speed of the pump 100 is decreased gradually, at a strategically-selected rate, from the first rotation speed w 1 to the second rotation speed $\omega 2$ from the time T0 to the time T1. The selected rate of pump speed decrease can be, for example, a particular linear rate or a particular non-linear rate. During the second segment 510b of the first portion 510, from the time T1 to the time T2, the blood pump 100 is operated at the second rotation speed $\omega 2$. Similarly, the second portion 520 includes a first segment 520a during which the speed of the blood pump 100 is increased gradually, at a strategically-selected rate, from the third rotation speed $\omega 3$ to the fourth rotation speed $\omega 4$ from the time T2 to the time T3. During the second segment 520b of the second portion 520, from the time T3 to the time T4, the blood pump 100 is operated at the fourth rotation speed $\omega 4$. If desired, at time T4, there is a step increase in the rotation speed of the rotor 140 can be rapidly increased to the first rotation speed w 1, and the pump speed pattern 500 is repeated.

The concept of creating multiple speed changes at a strategically-selected rate is based upon producing the physiologic response that is similar to that produced during human cardiac systole and diastole. For example, if very accurate matching of energy dissipation during a human pulse is necessary, the additional complexity of pattern 500 may be warranted.

The pump speed pattern 500 illustrates the difference between stepped transitions discussed above with respect to pump speed patterns 200-400, produced by rapidly changing the rotation speed of the rotor 140, and the gradual transitions of the first segment 510a of the first portion 510 and the first segment 520a of the second portion 520 of the pump speed pattern 500. Such gradual transitions can be included, for example, to mimic pressure changes exhibited during native diastole, as may be achieved by the gradual transition of the first segment 510a of the first portion 510 of the pump speed pattern 500. In some implementations, one or more of the rotation speed decreases of a pump speed pattern can be gradual transitions. For example, a pump speed pattern can include a gradual decrease in rotation speed from the first rotation speed ω1 to the third rotation speed ω3 and a stepped transition from the third pump speed ω3 back to the first rotation speed ω1. Various combinations of stepped and gradual transitions can be included in a pump speed pattern to produce a desired arterial pressure wave form, or other desired physiologic effect. Additionally, the type of transition between rotation speeds can affect power consumption of the blood pump 100, and the pump speed pattern can be selected based, at least in part, on power consumption considerations.

For all the pump speed patterns discussed it should be appreciated that although rotor speed is the technological parameter utilized to impart an artificial pulse, any physiologic effect is related to the consequential pressure and flow patterns, including pulse pressure, the maximum time variation in rate of blood pressure change (dp/dt), and the like. Rotor speed is not intrinsically physiologically meaningful. The human vascular system naturally dampens the native pulse produced by the heart, and it will do the same for an artificial pulse produced as described. The invention describes a utilitarian combination of factors that result in a physiological meaningful pulse. Thus, the pump speed patterns 200-500 described above are exemplary combinations of parameters that result in a physiologically meaningful pulse.

Figure 16:
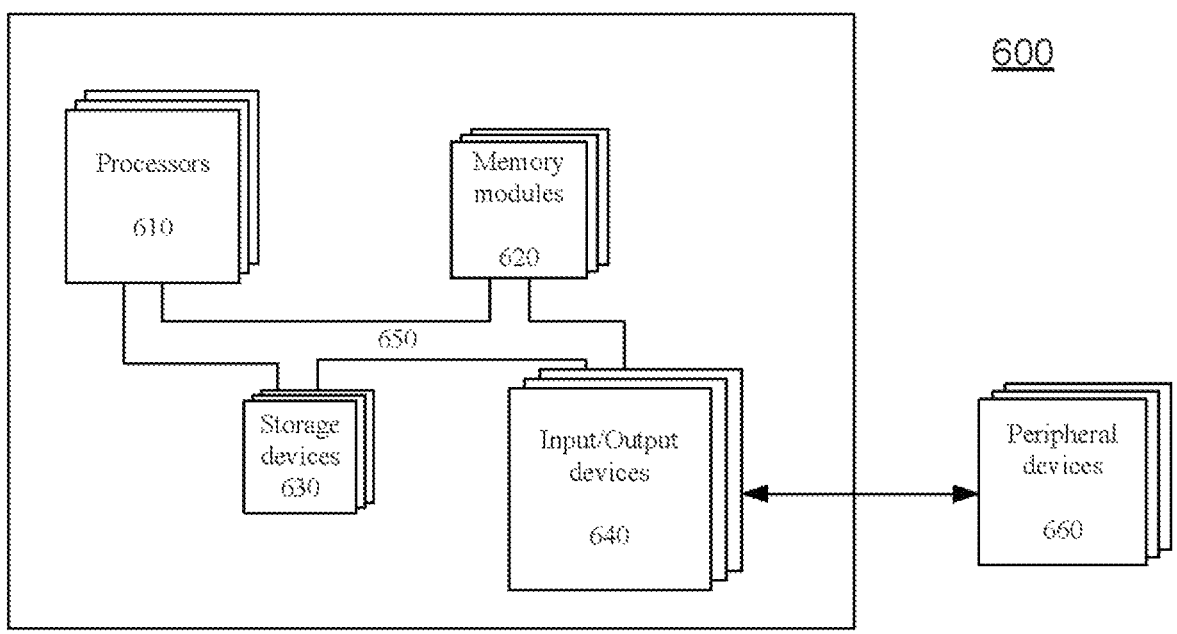
FIG. 16 is a diagram of a computer system.

In use, the pump speed patterns 200-500 can be generated by a controller that is configured to generate an electrical drive signal to operate the blood pump 100. For example, the controller can include a computer system 600, shown in FIG. 16, that outputs an electrical current to operate the blood pump 100. In order to produce the pump speed pattern 200 described above, the controller outputs a first electrical current from the time T0 to the time T1. At the time T1, the controller reduces the output electrical current to a second current that is lower than the first electrical current, and outputs the second electrical current from the time T1 to the time T2. At the time T2, the controller reduces the output electrical current from the second current to a third current, and outputs the third electrical current from the time T2 to the time T4.

The computer system 600 includes one or more processors 610, memory modules 620, storage devices 630, and input/output devices 640 connected by a system bus 650.

The input/output devices 640 are operable to communicate signals to, and/or receive signals from, one or more peripheral devices 660. For example, a peripheral device 660 can be used to store computer executable instructions on the memory modules 620 and/or the storage devices 630 that are operable, when executed by the processors, to cause the controller to generate a waveform to control the operation of the pump 100 and produce a pump speed pattern, such as the pump speed patterns 200-500.

Additionally, the controller can include a sensor that provides a signal that indicates activity of the heart H. For example, the controller can include a sensor that provides a signal indicative of power consumption of the blood pump 100. The signal can be used to determine when the left ventricle LV contracts. For example, the power consumption of the blood pump 100 may, for a given operating speed, increase as the left ventricle LV contracts. Based on the determined heart activity, the controller can adjust the generated control waveform. For example, the controller can automatically adjust the timing and duration of the first portion 210 and the second portion 220 of the pump speed pattern 200 such that the first portion 210 approximately coincides with a contraction of the left ventricle LV. The pump 100 is controlled such that the time T0 approximately coincides with a beginning of a contraction of the left ventricle LV and the time T2 approximately coincides with an end of the contraction of the left ventricle LV. The time T4 approximately coincides with a beginning of a subsequent contraction of the left ventricle LV. Thus, the durations of the various portions and/or segments of the pump speed patterns described above can be changed individually or collectively for one or more repetitions of the pump speed patterns. Using these techniques, the controller can synchronize the pulsatile operation of the blood pump 100 with the natural physiologic pulse of the heart H.

Alternatively, the controller can generate the control waveform independently of the activity of the heart H and/or to operate in opposition to the activity of the heart H, such as where the first portion 210 occurs during left ventricular relaxation. Similarly, the controller can generate a control waveform that includes a distinctly non-physiologic pulse rate, such as fewer than 40 high-pressure periods per minute, and the waveform can be generated independently of native heart function. In some examples, the blood pump 100 can be operated to produce distinctly physiologic pulse rates, such as between 50 and 110 high-pressure periods per minute, and can be controlled dependently or independently of heart function.

A number of implementations have been described. Nevertheless, it will be understood that various modifications may be made without departing from the spirit and scope of the claimed invention. For example, the pump speed patterns described above can be used with various types of blood pumps, including axial flow blood pumps and centrifugal flow blood pumps. Similarly, the rotors of blood pumps used to produce pulsatile blood flow patterns as described above may be electromagnetically-suspended, hydraulically-suspended, mechanically-suspended, or combinations thereof. The rotors may also partially be passively magnetically-suspended. However, the effect of an artificial pulse may most accurately be simulated by a pump in which the rotor is electromagnetically suspended, with or without partial passive magnetic suspension, because in general, other things being equal, electromagnetic suspension yields a high degree of responsiveness of the rotor to speed change inputs. For example, mechanical bearings associated with mechanical suspension and/or very narrow rotor clearance gaps associated with hydraulic suspension hinder rapid acceleration of the rotor compared to similar pumps that employ electromagnetic suspension. Additionally, while the pump speed patterns described above have been described with regard to a measure of angular velocity, the pump speed patterns can be produced with regard to one or more different measures of pump speeds. Additionally, there may be a delay between a change in drive signal generated by the controller and a change in operating speed of the blood pump. Thus, the controller can be operated such that changes in the output drive signal are effected at a time to produce a corresponding change in pump operating speed at a desired time, such as a time that approximately coincides with selected activity of the heart.

In some implementations, the pump speed patterns 200-500 can include additional portions or segments during which the blood pump is operated at other speeds. For example, at desired times, the blood pump can be operated to produce a pump speed pattern that produces a desired physiologic effect, such as opening or closing the aortic valve. Such operation of the blood pump can interrupt a generally continuous repetition of a selected one or more of the pump speed patterns described above, or others, including an indefinite period of constant speed, and a selected pump speed pattern can be resumed after the desired physiologic effect has been produced. The pump speed patterns 200-500 can also include different portions or segments. For example, the second segment 210b of the first portion 210 of the pump speed pattern 200 can include multiple pump speeds. Similarly, the transitions between pump speeds, such as the reduction in pump speed from the first rotation speed $\omega 1$ to the second rotation speed $\omega 2$, can include constant, variable, exponential, combinations thereof, or other rate of speed change over time such that the transition, such as the first segment 510a of the first portion 510 of the pump speed pattern 500, is linear, curvilinear, parabolic, logarithmic, sinusoidal, stepped, or combinations thereof.

In some implementations, one or more of the pump speed changes in the pump speed patterns 200-500 can be monotonic. A transition from one speed to another may occur gradually over a period of time, yet change directly from one speed to another. For example, to decrease a pump speed from a first rotational speed to a second rotational speed, the controller can reduce the pump speed without causing an intervening period of increasing pump speed. Similarly, the transition from the first rotational speed to the second rotational speed can occur without operating the pump above the first rotational speed during the transition.

Additionally, a blood pump can be operated according to a pump speed pattern that is selected according to a pump power consumption rate associated with the pump speed pattern, a pump efficiency associated with the pump speed pattern, a blood flow rate associated with the pump speed pattern, and/or a rate of blood pressure change associated with the pump speed pattern. For example, in a first mode, the controller can be operated to produce a pump speed pattern that produces a desired rate of blood pressure change. When a low power condition is detected, the controller can be switched to a power-saving mode to produce a pump speed pattern that has a low power consumption rate, even if the desired rate of pressure change is not produced in the power-saving mode.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis, such as where the patient's aortic valve is surgically sealed.

The subject matter and the functional operations described in this specification can be implemented in digital electronic circuitry, in tangibly-embodied computer software or firmware, in computer hardware, including the structures disclosed in this specification and their structural equivalents, or in combinations of one or more of them. The subject matter described in this specification can be implemented as one or more computer programs, i.e., one or more modules of computer program instructions encoded on a tangible non transitory program carrier for execution by, or to control the operation of, data processing apparatus. The program carrier can be a computer storage medium, for example, a machine-readable storage device, a machine-readable storage substrate, a random or serial access memory device, or a combination of one or more of them, as described further below. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read only memory or a random access memory or both. The essential elements of a computer are a processing unit for performing or executing instructions and one or more memory devices for storing instructions and data. A computer can also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a pump, a pump controller, or a portable storage device, e.g., a universal serial bus (USB) flash drive or other removable storage module, to name a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Accordingly, other embodiments are within the scope of the following claims.

What is claimed is:

1. A mechanical circulatory assist system comprising:
    a continuous-flow pump comprising a centrifugal rotor configured to generate a centrifugal flow, wherein the continuous-flow pump is adapted to pump blood from a left ventricle of a heart of a patient to an aorta of the patient to assist blood flow from the left ventricle to the aorta; and
    a controller comprising a sensor that generates a signal indicative of a power consumption of the continuous-flow pump, wherein the controller is operatively connected to the continuous-flow pump and configured to operate the continuous-flow pump in an artificial pulse mode comprising recurring changes in a rotational speed of the continuous-flow pump, wherein at least one of the recurring changes in the rotational speed of the continuous-flow pump are synchronized with contractions of the left ventricle, wherein the controller comprising a processor configured to detect, based on a speed of the continuous-flow pump and the power consumption of the continuous-flow pump, the contractions of the left ventricle.

2. The mechanical circulatory assist system of claim 1, wherein the continuous-flow pump comprises a stator that radially surrounds the centrifugal rotor and is operable to rotate the centrifugal rotor and radially levitate the centrifugal rotor using only passive and active magnetic forces.

3. The mechanical circulatory assist system of claim 2, wherein the stator comprises drive coils operable to rotate the centrifugal rotor and levitation coils operable to magnetically radially levitate the centrifugal rotor.

4. The mechanical circulatory assist system of claim 3, wherein the artificial pulse mode comprises:
    (a) operating the continuous-flow pump at a first speed for a first speed duration;
    (b) reducing the speed of the continuous-flow pump from the first speed to a second speed;
    (c) operating the continuous-flow pump at the second speed for a second speed duration;
    (d) reducing the speed of the continuous-flow pump from the second speed to a third speed;
    (e) operating the continuous-flow pump at the third speed for a third speed duration; and repeating steps (a) through (e).

5. The mechanical circulatory assist system of claim 4, wherein the controller operates the continuous-flow pump at the first speed during the contractions of the left ventricle.

6. The mechanical circulatory assist system of claim 5, wherein the controller controls at least one of the first speed duration, the second speed duration, and the third speed duration to synchronize operation of the continuous-flow pump in the artificial pulse mode with the contractions of the left ventricle.

7. The mechanical circulatory assist system of claim 6, wherein each of the first speed durations begins at a start of a respective contraction of the left ventricle.

8. The mechanical circulatory assist system of claim 7, wherein each of the first speed durations ends approximately at an end of the respective contraction of the left ventricle.

9. The mechanical circulatory assist system of claim 4, wherein the controller operates the continuous-flow pump at the first speed during relaxation of the left ventricle.

10. The mechanical circulatory assist system of claim 4, wherein the artificial pulse mode further comprises returning the speed of the continuous-flow pump from the third speed to the first speed by overshooting the first speed to a greater speed before returning to the first speed.

11. A method of controlling a continuous-flow ventricular assist device, the method comprising:
    generating, by a sensor, a signal indicative of indicative of a power consumption of a continuous-flow ventricular assist device comprising a centrifugal rotor configured to generate a centrifugal flow, wherein the continuous-flow ventricular assist device receives blood from a ventricle of a heart of a patient and pumps the blood to an aorta of the patient to assist blood flow from the ventricle to the aorta;
    detecting, by a controller based on a speed of the continuous-flow ventricular assist device and the power consumption of the continuous-flow ventricular assist device, contractions of the ventricle; and
    controlling, by the controller, the speed of the continuous-flow ventricular assist device to operate in an artificial pulse mode that produces a pulsatile blood flow, wherein the artificial pulse mode comprises recurring changes in a rotational speed of the continuous-flow ventricular assist device, and wherein at least one of the recurring changes in the rotational speed of the continuous-flow ventricular assist device are synchronized with the contractions of the ventricle.

12. The method of claim 11, wherein the continuous-flow ventricular assist device comprises a stator that radially surrounds the centrifugal rotor and is operable to rotate the centrifugal rotor and radially levitate the centrifugal rotor using only passive and active magnetic forces.

13. The method of claim 12, wherein the stator comprises drive coils operable to rotate the centrifugal rotor and levitation coils operable to magnetically radially levitate the centrifugal rotor.

14. The method of claim 11, wherein the artificial pulse mode comprises:
    (a) operating the continuous-flow ventricular assist device at a first speed for a first speed duration;
    (b) reducing the speed of the continuous-flow ventricular assist device from the first speed to a second speed;
    (c) operating the continuous-flow ventricular assist device at the second speed for a second speed duration;

(d) reducing the speed of the continuous-flow ventricular assist device from the second speed to a third speed;

(e) operating the continuous-flow ventricular assist device at the third speed for a third speed duration; and repeating steps (a) through (e).

15. The method of claim 14, wherein the controller operates the continuous-flow ventricular assist device at the first speed during the contractions of the ventricle.

16. The method of claim 15, wherein the controller controls at least one of the first speed duration, the second speed duration, and the third speed duration to synchronize operation of the continuous-flow ventricular assist device in the artificial pulse mode with the contractions of the ventricle.

17. The method of claim 16, wherein each of the first speed durations begins at a start of a respective contraction of the ventricle.

18. The method of claim 17, wherein each of the first speed durations ends approximately at an end of the respective contraction of the ventricle.

19. The method of claim 14, wherein the controller operates the continuous-flow ventricular assist device at the first speed during relaxation of the ventricle.

20. The method of claim 14, wherein the artificial pulse mode further comprises returning the speed of the continuous-flow ventricular assist device from the third speed to the first speed by overshooting the first speed to a greater speed before returning to the first speed.

21. The mechanical circulatory assist system of claim 1, wherein:

the continuous-flow pump comprises a housing that defines an inlet cannula, an outlet opening, and a blood flow channel that fluidly connects the outlet opening with the inlet cannula; and the inlet cannula is configured to extend into the left ventricle.

22. The mechanical circulatory assist system of claim 4, wherein the artificial pulse mode is configured to produce a rate of blood pressure change in a range from 500 to 1000 mmHG per second.

23. The method of claim 11, wherein the continuous-flow ventricular assist device comprises a housing that defines an inlet cannula that extends into the ventricle.

24. The method of claim 14, wherein a rate of blood pressure change produce by the continuous-flow ventricular assist device in the artificial pulse mode is in a range from 500 to 1000 mmHG per second.

25. A mechanical circulatory assist system comprising:

a continuous-flow pump comprising a centrifugal rotor configured to generate a centrifugal flow, wherein the continuous-flow pump is adapted to pump blood from a left ventricle of a heart of a patient to an aorta of the patient to assist blood flow from the left ventricle to the aorta; and a controller comprising a sensor that generates a signal indicative of a power consumption of the continuous-flow pump, wherein the controller is operatively connected to the continuous-flow pump and configured to operate the continuous-flow pump in an artificial pulse mode synchronized with contractions of the left ventricle, wherein the artificial pulse mode is configured to produce a rate of blood pressure change in a range from 500 to 1000 mmHG per second, wherein the controller comprising a processor configured to detect, based on a speed of the continuous-flow pump and the power consumption of the continuous-flow pump, the contractions of the left ventricle.

26. The mechanical circulatory assist system of claim 25, wherein the artificial pulse mode comprises recurring changes in a rotational speed of the continuous-flow pump, wherein at least one of the recurring changes in the rotational speed of the continuous-flow pump are synchronized with the contractions of the left ventricle.

* * * * *